United States Patent
Tsutsuminai et al.

(10) Patent No.: US 8,445,731 B2
(45) Date of Patent: May 21, 2013

(54) PROCESS FOR PRODUCING BISPHENOL COMPOUND

(75) Inventors: Susumu Tsutsuminai, Ibaraki (JP); Kazuaki Kanno, Ibaraki (JP); Makiko Tachikura, Ibaraki (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 13/187,066

(22) Filed: Jul. 20, 2011

(65) Prior Publication Data

US 2012/0010434 A1   Jan. 12, 2012

Related U.S. Application Data

(63) Continuation of application No. PCT/JP2010/050736, filed on Jan. 21, 2010.

(30) Foreign Application Priority Data

| Jan. 22, 2009 | (JP) | P. 2009-012223 |
| Dec. 7, 2009 | (JP) | P. 2009-277749 |
| Dec. 10, 2009 | (JP) | P. 2009-280651 |
| Dec. 11, 2009 | (JP) | P. 2009-281781 |

(51) Int. Cl.
*C07C 39/12* (2006.01)

(52) U.S. Cl.
USPC ........................................ 568/727

(58) Field of Classification Search
None
See application file for complete search history.

(56) References Cited

U.S. PATENT DOCUMENTS

| 4,423,252 A * | 12/1983 | Maki et al. .................. 568/728 |
| 4,478,956 A | 10/1984 | Maki et al. |
| 6,534,686 B1 | 3/2003 | Webb et al. |
| 6,620,939 B2 | 9/2003 | Webb et al. |
| 6,667,402 B2 | 12/2003 | Sato et al. |
| 2003/0211934 A1 | 11/2003 | Hayashi et al. |
| 2003/0234381 A1 | 12/2003 | Hayashi |
| 2006/0041145 A1 | 2/2006 | Hayashi et al. |

FOREIGN PATENT DOCUMENTS

| CN | 1764643 | 4/2006 |
| JP | 53-144577 | 12/1978 |
| JP | 57-32240 | 2/1982 |
| JP | 57-35533 | 2/1982 |
| JP | 6-296871 | 10/1994 |
| JP | 08-187436 | 7/1996 |
| JP | 11-228540 | 8/1999 |
| JP | 11-246458 | 9/1999 |
| JP | 11-255748 | 9/1999 |
| JP | 2001-503377 | 3/2001 |
| JP | 2001-316313 | 11/2001 |
| JP | 2001-335522 | 12/2001 |
| JP | 2002-069023 | 3/2002 |
| JP | 2002-177797 | 6/2002 |
| JP | 2002-205966 | 7/2002 |
| JP | 2002-220373 | 8/2002 |
| JP | 2002-255882 | 9/2002 |
| JP | 2005-60371 | 3/2005 |
| JP | 2005-170820 | 6/2005 |
| JP | 2005-239872 | 9/2005 |
| JP | 2008-273951 | 11/2008 |
| WO | WO 97/22573 | 6/1997 |
| WO | WO 2008/120666 A1 | 10/2008 |

OTHER PUBLICATIONS

International Search Report issued Apr. 6, 2010 in PCT/JP2010/050736 filed Jan. 21, 2010.
Kagaku Daijiten Henshu linkai, Kagaku Daijiten 7 reduced-size edition, Kyoritsu Shuppen Co., Ltd., 1964, pp. 481-482.
Ludwig Bauer et al.; "Addition of Thiourea to 2- and 4-Vinylpyridines"; Journal of Organic Chemistry, 1961, vol. 26, pp. 82-85.
Extended European Search Report issued Jun. 28, 2012, in European Patent Application No. 10733536.6.
Office Action issued in Chinese Application No. 201080005481.5 mailed Apr. 3, 2013 w/English translation.

* cited by examiner

*Primary Examiner* — Sudhakar Katakam
(74) *Attorney, Agent, or Firm* — Oblon, Spivak, McClelland, Maier & Neustadt, L.L.P.

(57) ABSTRACT

Provided is a process for producing a bisphenol compound stably at a high conversion and with high selectivity over a long period. A process for producing a bisphenol compound by feeding a phenol compound and a carbonyl compound continuously to a reactor packed with an acid catalyst, characterized in that the acid catalyst is a sulfonic-acid-form cation-exchange resin in which part of the sulfo groups have been modified with at least any one of 2-pyridylalkanethiol compounds and 3-pyridylalkanethiol compounds.

45 Claims, 4 Drawing Sheets

PROCESS FOR PRODUCING BISPHENOL COMPOUND

TECHNICAL FIELD

The present invention relates to a process for producing a bisphenol compound. More particularly, the invention relates to a process for bisphenol compound production which is characterized in that a sulfonic-acid-form cation-exchange resin in which the sulfo groups have been partly modified with a pyridylalkanethiol compound having a specific structure is used as an acidic catalyst.

BACKGROUND ART

Process for Producing Bisphenol Compounds

Bisphenol compounds are generally produced by the condensation reaction of a phenol compound with a carbonyl compound in the presence of an acidic catalyst. Cation-exchange resins having acidic groups such as sulfo groups are widely used as the acidic catalyst, although mineral acids such as hydrochloric acid and sulfuric acid and solid acids such as heteropolyacids are also used. It is known that the reactants are reacted while causing a compound having a thiol group or a protected thiol group (hereinafter often referred to as "thiol compound") to coexist with a catalyst for the purpose of improving conversion, selectivity, etc.

Methods for causing a thiol compound to coexist with a catalyst include: (1) a method in which a thiol compound is continuously supplied to an acidic catalyst together with a phenol compound and a carbonyl compound, which are starting materials, and reacted (see, for example, patent documents 1 and 2); and (2) a method in which the sulfo groups of a sulfonic-acid-form cation-exchange resin are modified, prior to reaction, with a thiol compound having a functional group, e.g., an amino group, that is capable of combining with a sulfo group (e.g., an aminoalkanethiol compound or a pyridylalkanethiol compound) and the modified cation-exchange resin is used for the reaction (see, for example, patent documents 3 to 6).

The method (2), in which a sulfonic-acid-form cation-exchange resin modified with a thiol compound is used as an acidic catalyst, is superior to the method (1), in which a thiol compound is continuously supplied to an acidic catalyst together with starting materials, because the method (2) has advantages, for example, that the thiol compound does not come into the reaction product and, hence, there is no need of recovering the compound, and that catalyst preparation is easy.

Various compounds including aminoalkanethiol compounds and pyridylalkanethiol compounds are known as thiol compounds usable for modifying sulfonic-acid-form cation-exchange resins. Of such compounds, pyridylalkanethiol compounds are known to show excellent performance with respect to conversion and selectivity (see, for example, patent documents 4 to 6).

Patent document 4 describes Examples in which catalysts obtained by modifying a sulfonic-acid-form cation-exchange resin with various pyridylalkanethiol compounds were used to produce a bisphenol compound through a batch reaction. Patent document 2 shows that when 4-pyridylethanethiol among pyridylalkanethiols was used, the catalysts have satisfactory initial activity (conversion and selectivity in two hours from reaction initiation). However, no investigation has been made therein on the catalytic activity in long-term use of the various investigated catalysts, that activity being necessary when industrial use is supposed.

Patent documents 5 and 6 describe that use of a catalyst obtained by modifying a sulfonic-acid-form cation-exchange resin with 4-pyridylethanethiol was evaluated through a 500-hour reaction. However, no investigation has been made therein on use of catalysts obtained by modification with other pyridylalkanethiols.

In the case where an acidic catalyst obtained by modifying a sulfonic-acid-form cation-exchange resin with a pyridylalkanethiol compound is used to industrially produce a bisphenol compound, it is important to attain conversion of the starting materials during the reaction, selectivity to the bisphenol compound, and long-term stabilization of catalytic activity. However, a catalyst having higher performance is currently being desired for industrial production.

Process for Producing Pyridylethanethiol Compound

Many proposals have hitherto been made on methods for obtaining a pyridylethanethiol compound to be used for modifying a sulfonic-acid-form cation-exchange resin in producing a bisphenol compound. For example, a process for producing a pyridylethanethiol compound by reacting a vinylpyridine with a sulfur-containing compound is known (see, for example, patent documents 7 to 13 and non-patent document 1).

Patent documents 7 and 8 describe a process in which thioacetic acid is used as a sulfur-containing compound and a vinylpyridine is reacted with thioacetic acid to obtain pyridylethyl thioacetate as a pyridylethanethiol compound.

Incidentally, pyridylethyl thioacetate can be easily decomposed into pyridylethanethiol in the presence of an acid. However, this acetate, which is in the form of a derivative having a mercapto group protected with an acetyl group, can be used, as such, as a modifier for a catalyst to be used when bisphenol A is produced by the condensation of phenol with acetone.

Patent document 9 describes a process in which hydrogen sulfide is used as a sulfur-containing compound and a vinylpyridine is reacted with hydrogen sulfide to obtain a pyridylethanethiol as a pyridylethanethiol compound.

However, there is a problem that when a vinylpyridine and a sulfur-containing compound are used as starting materials to produce a pyridylethanethiol compound in accordance with the processes described in patent documents 7 to 9, the yield of the pyridylethanethiol compound is unexpectedly low.

Incidentally, investigations have conventionally been made on pretreatments, e.g., simple distillation, for removing coloring matter and impurities from vinylpyridines to be used as starting materials for producing pyridylethanethiol compounds. However, no investigation has been made from the standpoints of improving the yield of a pyridylethanethiol compound and preventing scale formation or deposition within production equipment. Such problems have not been overcome so far.

Known as a general process for producing a vinylpyridine, which is one of starting materials for producing pyridylethanethiol compounds, is a process in which a picoline and formaldehyde are subjected to a methylolation reaction to yield a 2-pyridylethanol, e.g., 2-(4-pyridyl)ethanol or 2-(2-pyridyl)ethanol, and the 2-pyridylethanol is subjected to a dehydration reaction in the presence of an alkali (see, for example, patent document 10).

The vinylpyridine produced is purified, for example, by distillation. However, the product contains several kinds of impurities. These impurities include the picoline, which is the starting material remaining unreacted, by-products including ethylpyridine, isopropenylpyridine, propenylpyridine, methylvinylpyridines, in which a methyl group and a vinyl group have been bonded to the pyridine framework, homopolymers which are the dimer and higher polymers of the vinylpyridine, etc.

Also known as a process for producing a pyridylethanethiol compound is a process in which a vinylpyridine is reacted with thiourea, which is a sulfur-containing compound, in an ethanol solvent to obtain an isothiuronium salt and the isothiuronium salt obtained is hydrolyzed to obtain a pyridylethanethiol (see, for example, non-patent document 1 and patent documents 11 to 14).

Non-patent document 1 describes a process in which 4-vinylpyridine is reacted with thiourea, which is a sulfur-containing compound, in an ethanol solvent in the presence of p-toluenesulfonic acid to yield an isothiuronium salt and the isothiuronium salt is subsequently converted to 4-pyridylethanethiol in ammonium water. In patent documents 11 and 12 is described an invention which is an improvement of that process.

Patent document 13 describes a process in which a reaction for yielding an isothiuronium salt is conducted in an aqueous solvent and the liquid reaction mixture resulting from the reaction is reacted with an aqueous ammonia solution to thereby easily produce 4-pyridylethanethiol without isolating the isothiuronium salt.

However, such conventional processes have drawbacks that when the isothiuronium salt is hydrolyzed to produce a thiol compound, polymers are formed as by-products, resulting in a decrease in yield, and that the polymers formed in the production apparatus adhere as solid matter to cause apparatus fouling. Furthermore, the adhesion of solid matter poses a problem concerning liquid transfer troubles and clogging of the piping. There also is a problem that the adhered solid matter constitutes an obstacle to the operation for recovering the target substance through extraction after the reaction.

Patent document 14 proposes a process for producing a thiol compound in high yield by hydrolyzing an isothiuronium salt in an aqueous alkali solution while inhibiting the formation of by-product polymers, wherein the hydrolysis of the isothiuronium salt is conducted in the presence of a water-insoluble organic solvent, e.g., toluene.

According to the process proposed in patent document 14, the formation of by-product polymers during the hydrolysis of the isothiuronium salt can be inhibited to attain an improvement in yield. However, the improvement is not sufficient.

Furthermore, in the conventional processes for producing a pyridylethanethiol compound, there has been a problem that the equipment for pyridylethanethiol compound production is fouled (scale formation on inner walls of the apparatus) as a result of continuous operation. In severe cases, clogging of the piping occurs to make continuous operation of the apparatus impossible, resulting in the necessity of stopping the operation and conducting a cleaning operation for removing the solid matter deposited in the apparatus. There has hence been a problem that the processes frequently require a maintenance operation, i.e., have a low efficiency of apparatus operation, and further have a poor production efficiency.

Thiol Group of Thiol Compound

The thiol compound to be used for modifying a sulfonic-acid-form cation-exchange resin in producing a bisphenol compound has a problem that the thiol group thereof is readily oxidized under the conditions used in the synthesis thereof and under conditions used when the compound is used as a modifier, and the thiol compound is thereby converted to a disulfide. This deterioration of the thiol compound through oxidation of the thiol group can be prevented by protecting the thiol group of the thiol compound with an acyl group (see, for example, patent documents 15 and 16).

Patent document 15 shows that when a pyridylalkanethiol compound in which the thiol group has been protected with an ester group or the like is used, the thiol group can be inhibited from being oxidized. The patent document includes an Example in which an acidic catalyst obtained by modifying part of the sulfo groups of a strongly acidic cation-exchange resin with the pyridylalkanethiol compound having a protected thiol group was used as such in molten phenol to produce bisphenol A.

However, in the process described in patent document 15, the protective group used for thiol group protection is dissociated during the reaction and an impurity, such as a carboxylic acid, derived from the protective group comes into the reaction product to pose problems such as those which will be described later.

Patent document 16 shows that an acidic ion exchanger which has undergone a modification reaction in which the ion exchanger is brought into contact with an emulsion-state pyridylalkanethiol compound improves the conversion of acetone when bisphenol A is produced by the condensation reaction of phenol with acetone. The patent document includes an Example in which a catalyst obtained by modifying part of a cation exchanger in an emulsion state pyridylalkanethiol compound in water at room temperature was used to produce bisphenol A.

For example, in the Example 2 of patent document 16, 4-pyridylethyl thioacetate was used as a modifier to conduct modification at room temperature and, after the modification, a complicated washing operation was conducted in which water was used in an amount at least 10 times (100 g×5) the amount of the water (40 g) used for the modification.

As described in patent documents 15 and 16, by protecting the thiol group of a thiol compound with an acyl group, not only the thiol compound can be prevented from deteriorating but also the odor which is characteristic of thiol compounds can be prevented. Consequently, the efficiency of thiol group introduction during the modification of a cation-exchange resin and the working environment therefor can be improved. However, the compound used for the modification, which was obtained by protecting the thiol group of a thiol compound with an acyl group, has a drawback that although this compound readily decomposes in the reaction system for bisphenol compound production to reproduce the thiol group, which is effective as a promoter for bisphenol compound production, the ester bond cleaved by the hydrolysis results in the formation of a carboxylic acid therefrom as a by-product.

Because of this, when a cation-exchange resin modified with the compound obtained by protecting the thiol group of a thiol compound with an acyl group is used as such for the production of a bisphenol compound, as in the process described in patent document 15, a carboxylic acid is liberated through hydrolysis in the reaction system. This acid ingredient is causative of apparatus corrosion. In addition, the liberated carboxylic acid and carboxylic acid esters, e.g., the phenyl carboxylate, formed by the reaction of the liberated carboxylic acid with a starting material come as impurities into the bisphenol compound production system. Furthermore, the carboxylic acid accelerates decomposition of the target bisphenol compound and accelerates formation of undesirable isomers (e.g., a 2,4'-bisphenol compound), thereby forming a main cause of impaired product quality.

One of the important uses of the polycarbonate resins produced from bisphenol compounds as starting materials is in optical applications. For use in these applications, polycarbonate resins especially having an excellent hue with no coloration or the like are required. Consequently, in order to produce polycarbonate resins which meet that requirement, bisphenol compounds which have a high purity and contain no impurities including coloring matter must be used as starting materials. However, processes in which a cation-exchange resin modified with the compound obtained by protecting the thiol group of a thiol compound with an acyl group is used, as such, as a catalyst for bisphenol compound production, like the process described in patent document 15, cannot meet the quality requirement.

Meanwhile, in the process described in patent document 16, it is necessary that a complicated cleaning operation using a large amount of water should be conducted in a plurality of times in order to prevent the carboxylic acid hydrolytically formed as a by-product from coming into the bisphenol compound production system. This process is hence unsuitable for industrial production. In the case where water is not used in a large amount, the carboxylic acid hydrolytically formed as a by-product comes into the reaction system for bisphenol compound production, as in the process described in patent document 15, to pose the same problems as in the process described in patent document 15.

With respect to methods for removing the carboxylic acid which has come into the reaction system, patent document 17, for example, proposes a method in which the step of removing the free acid using an adsorbent is conducted. However, it is necessary to newly install an apparatus for free-acid removal, and this method is difficult to apply to existing equipment.

PRIOR-ART DOCUMENTS

Patent Documents

Patent Document 1: JP-T-2001-503377
Patent Document 2: JP-A-2002-205966
Patent Document 3: JP-A-08-187436 (1996)
Patent Document 4: JP-A-57-35533 (1982)
Patent Document 5: JP-A-11-246458 (1999)
Patent Document 6: JP-A-2002-69023
Patent Document 7: U.S. Pat. No. 6,534,686
Patent Document 8: U.S. Pat. No. 6,620,939
Patent Document 9: U.S. Pat. No. 6,667,402
Patent Document 10: JP-A-53-144577 (1978)
Patent Document 11: JP-A-11-228540 (1999)
Patent Document 12: JP-A-11-255748 (1999)
Patent Document 13: JP-A-2002-220373
Patent Document 14: JP-A-2005-170820
Patent Document 15: U.S. Pat. No. 6,534,686
Patent Document 16: JP-A-2005-239872
Patent Document 17: JP-A-2001-316313

Non-Patent Document

Non-Patent Document 1: *J. Org. Chem.*, 26, 82 (1961)

SUMMARY OF THE INVENTION

Problems that the Invention is to Solve

An object of the invention, which overcomes the problems described above, is to provide an industrially advantageous process for producing a bisphenol compound by continuously reacting a phenol compound with a carbonyl compound using as an acidic catalyst a sulfonic-acid-form cation-exchange resin modified with a thiol compound, wherein the target bisphenol compound can be produced with high selectivity while maintaining a high conversion over a long period.

Another object of the invention is to enable a 2-pyridylethanethiol compound for modifying a sulfonic-acid-form cation-exchange resin to be obtained from 2-vinylpyridine and a sulfur-containing compound as starting materials so that the 2-pyridylethanethiol is obtained in high yield and that problems encountered in the production equipment, such as scale formation and clogging of the piping, are prevented to improve operation efficiency and production efficiency.

Still another object of the invention is to provide a method for industrially advantageously obtaining an acidic catalyst without requiring a complicated operation or a special apparatus, the acidic catalyst being capable of eliminating the problem that impurities which are derived from the compound obtained by protecting the thiol group of a thiol compound with an acyl group and used for modifying a sulfonic-acid-form cation-exchange resin come into the reaction system for bisphenol compound production.

Means for Solving the Problems

The present inventors diligently made investigations in order to overcome the problems described above. As a result, the inventors have found that by using a sulfonic-acid-form cation-exchange resin modified with at least any one of 2-pyridylalkanethiol compounds and 3-pyridylalkanethiol compounds, which have been regarded as substantially equal or inferior in initial activity to 4-pyridylalkanethiols according to the known investigations described in, for example, patent document 2, as an acidic catalyst in the continuous production of a bisphenol compound, the bisphenol compound can be produced with high selectivity while maintaining a higher conversion over a longer period than in the case where a sulfonic-acid-form cation-exchange resin modified with a 4-pyridylalkanethiol is used as an acidic catalyst.

Furthermore, the inventors have found that when 2-pyridylethanethiol to be used for modifying a sulfonic-acid-form cation-exchange resin is obtained from 2-vinylpyridine and a sulfur-containing compound as starting materials, then the dimer and higher polymers of 2-vinylpyridine are formed during the synthesis of the 2-vinylpyridine and during subsequent storage thereof and come as impurities into the 2-vinylpyridine. These polymers not only reduce the yield of 2-pyridylethanethiol but also are causative of scale deposition within the production apparatus. The inventors have found that these problems can be overcome by regulating the amount of such polymers contained in the 2-vinylpyridine.

Moreover, in the case where 2-pyridylethanethiol to be used for modifying a sulfonic-acid-form cation-exchange resin is obtained by reacting 2-vinylpyridine with thiourea to obtain an isothiuronium salt and hydrolyzing the isothiuronium salt obtained, those problems can be overcome by synthesizing the isothiuronium salt in the presence of water and a hydrocarbon solvent.

In addition, the inventors have found that when a compound which has been obtained from at least any one of 2-pyridylalkanethiol compounds and 3-pyridylalkanethiol compounds by protecting the thiol group thereof with an acyl group and which is to be used for modifying a sulfonic-acid-form cation-exchange resin is subjected to hydrolysis of the thioester moiety thereof at a temperature higher than room temperature, then the hydrolysis can be efficiently conducted in a short period while maintaining catalytic performance. It has been thus found that the problems concerning deterioration due to oxidation of the thiol group and concerning odor can be overcome, and that it is possible to obtain an acidic catalyst which is free from the problem that carboxylic acid ingredients formed by the hydrolysis of the thioester moiety come into the reaction system for bisphenol compound production.

The invention has been completed based on these findings. Specifically, the invention is as follows.

1. A process for producing a bisphenol compound which comprises feeding a phenol compound and a carbonyl compound to a reactor packed with an acidic catalyst to produce the bisphenol compound, characterized in that the acidic catalyst is a sulfonic-acid-form cation-exchange resin in which part of the sulfo groups have been modified with at least any one of 2-pyridylalkanethiol compounds and 3-pyridylalkanethiol compounds and that the phenol compound and the carbonyl compound are continuously fed to the reactor packed with the acidic catalyst.

2. The process for producing a bisphenol compound according to 1 above wherein the acidic catalyst is a sulfonic-acid-form cation-exchange resin in which part of the sulfo groups have been modified with a 2-pyridylalkanethiol compound.

3. The process for producing a bisphenol compound according to 1 or 2 above wherein the 2-pyridylalkanethiol compound(s) is 2-pyridylethanethiol.

4. The process for producing a bisphenol compound according to 3 above wherein the 2-pyridylethanethiol is 2-pyridylethanethiol obtained from 2-vinylpyridine and a sulfur-containing compound as starting materials, and the content in the 2-vinylpyridine of 2-vinylpyridine-containing polymers which are the dimer and higher polymers is 2% by weight or less.

5. The process for producing a bisphenol compound according to 4 above wherein the content in the 2-vinylpyridine of 2-vinylpyridine-containing polymers which are the dimer and higher polymers is 100 weight ppm or higher.

6. The process for producing a bisphenol compound according to 4 or 5 above wherein the sulfur-containing compound is thiourea.

7. The process for producing a bisphenol compound according to 3 or 6 above wherein the 2-pyridylethanethiol is 2-pyridylethanethiol obtained by reacting 2-vinylpyridine with thiourea in the presence of water and a hydrocarbon solvent to obtain an isothiuronium salt and hydrolyzing the isothiuronium salt.

8. The process for producing a bisphenol compound according to 7 above wherein the hydrocarbon solvent is toluene.

9. The process for producing a bisphenol compound according to 1 above wherein the acidic catalyst is a sulfonic-acid-form cation-exchange resin in which part of the sulfo groups have been modified with a 3-pyridylalkanethiol compound.

10. The process for producing a bisphenol compound according to 1 or 9 above wherein the 3-pyridylalkanethiol compound(s) is 3-pyridylethanethiol.

11. The process for producing a bisphenol compound according to any one of 2, 3, 4, 5, 9, and 10 above wherein the acidic catalyst is an acidic catalyst obtained through the following steps (I) and (II):

(I) a modification step in which a sulfonic-acid-form cation-exchange resin is modified using a compound obtained by protecting the thiol group of at least any one of 2-pyridylalkanethiol compounds and 3-pyridylalkanethiol compounds with an acyl group;

(II) a hydrolysis step in which the thioester moiety of the compound obtained by protecting the thiol group of at least any one of 2-pyridylalkanethiol compounds and 3-pyridylalkanethiol compounds with an acyl group is hydrolyzed at a temperature of 40° C. to 100° C. during the modification and/or after the modification.

12. The process for producing a bisphenol compound according to 11 above wherein in step (II), the conversion in hydrolysis of the compound obtained by protecting the thiol group of at least any one of 2-pyridylalkanethiol compounds and 3-pyridylalkanethiol compounds with an acyl group is 60% or higher.

13. The process for producing a bisphenol compound according to any one of 1 to 12 above wherein the phenol compound is phenol, the carbonyl compound is acetone, and the bisphenol compound is bisphenol A.

14. The process for producing a bisphenol compound according to any one of 1 to 13 above wherein at least part of the phenol compound is a phenol compound obtained when a bisphenol compound was purified.

EFFECTS OF THE INVENTION

According to the process of the invention, in which a sulfonic-acid-form cation-exchange resin modified with at least any one of 2-pyridylalkanethiol compounds and 3-pyridylalkanethiol compounds is used as an acidic catalyst to continuously react a phenol compound with a carbonyl compound and thereby produce a bisphenol compound, the bisphenol compound can be continuously produced stably with high conversion and high selectivity over a prolonged period. This process is industrially exceedingly advantageous.

Especially when at least part of the phenol compound is a phenol compound which was obtained when a bisphenol compound was purified, then there are the cases where compounds which are not the necessary phenol compound are also supplied to the reactor to deactivate the catalyst. Even in such cases, the process of the invention enables the bisphenol compound to be continuously produced stably with high conversion and high selectivity over a prolonged period.

Furthermore, according to the process of the invention, in the case where the 2-pyridylethanethiol for modifying a sulfonic-acid-form cation-exchange resin is to be obtained from 2-vinylpyridine and a sulfur-containing compound as starting materials, the 2-vinylpyridine may be one in which the content of 2-vinylpyridine-containing polymers which are the dimer and higher polymers is 2% by weight or less. By using this 2-vinylpyridine, the yield of the 2-pyridylethanethiol compound can be improved.

Moreover, according to the process of the invention, in the case where the 2-pyridylethanethiol for modifying a sulfonic-acid-form cation-exchange resin is to be obtained by reacting 2-vinylpyridine with thiourea to obtain an isothiuronium salt and hydrolyzing the isothiuronium salt obtained, the reaction between 2-vinylpyridine and thiourea may be conducted in the presence of water and a hydrocarbon solvent. Thus, the yield of 2-pyridylethanethiol can be improved.

In addition, according to the process of the invention, not only the yield of 2-pyridylethanethiol is improved, but also the precipitation and formation of solid matter in the equipment for 2-pyridylethanethiol production are prevented and such solid matter is prevented from adhering to the inner walls of the apparatus or accumulating in corners or narrow parts and thereby arousing a problem concerning liquid transfer troubles or clogging of the piping. Consequently, the frequency of a maintenance operation in which the apparatus is stopped and the scale within the apparatus is removed is reduced, and the efficiency of apparatus operation is improved. As a result of the reduction in the frequency of a maintenance operation and the improvement in operation efficiency, it becomes possible to attain a reduction in cost and an improvement in production efficiency.

According to the process of the invention, the thioester moiety of the compound obtained by protecting the thiol group of at least any one of 2-pyridylalkanethiol compounds and 3-pyridylalkanethiol compounds with an acyl group and used for modifying a sulfonic-acid-form cation-exchange resin may be hydrolyzed at a temperature higher than room temperature, specifically, at 40-100° C. This hydrolysis can hence be efficiently carried out in a short period. Consequently, the problems concerning deterioration due to oxidation of the thiol group and odor are eliminated, and the thioester moiety is sufficiently hydrolyzed. As a result, it is possible to obtain an acidic catalyst reduced in the amount of a carboxylic acid ingredient formed by hydrolysis of the thioester moiety and coming into the reaction system for bisphenol compound production.

Furthermore, by using the compound obtained by protecting the thiol group of at least any one of 2-pyridylalkenethiol compounds and 3-pyridylalkanethiol compounds with an acyl group as a modifier and by conducting the hydrolysis during the modification or after the modification at a higher temperature than in conventional processes, the process can be easily practiced without requiring a special apparatus or a complicated operation.

Incidentally, when the compound obtained by protecting the thiol group of at least any one of 2-pyridylalkenethiol compounds and 3-pyridylalkanethiol compounds with an acyl group is used as a modifier, not only the thiol group can be prevented from being oxidized during storage of the modifier and during the modification, but also the odor which is characteristic of thiol compounds can be prevented. This process is hence superior in the efficiency of thiol group introduction during the modification of a sulfonic-acid-form cation-exchange resin and in the working environment therefor.

When the acidic catalyst obtained by the method described above is used, a carboxylic acid ingredient is inhibited from hydrolytically generating in the reaction system for bisphenol compound production. Consequently, according to this acidic catalyst, the problem that an acid ingredient formed in the reaction system for bisphenol compound production causes apparatus corrosion or impairs product quality is eliminated. Namely, that acidic catalyst does not pose problems such as inclusion of impurities, for example, the carboxylic acid and carboxylic acid esters, e.g., the phenyl carboxylate, formed by the reaction of the carboxylic acid with the phenol compound used as a starting material, decomposition of the target bisphenol compound by the action of the carboxylic acid, and a decrease in the purity of the target substance due to the formation of isomers represented by a 2,4'-bisphenol compound. Thus, the bisphenol compound of high quality can be efficiently produced.

MODES FOR CARRYING OUT THE INVENTION

Figure 1:
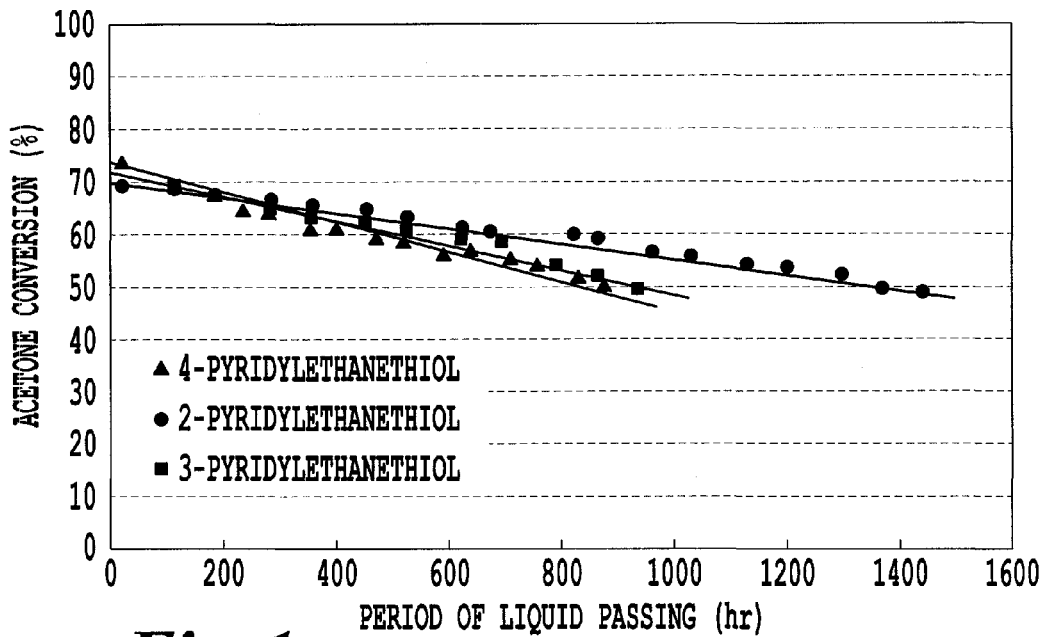
FIG. 1 is a presentation showing the changes with time of the conversion of acetone which were observed in Examples 1-1 and 1-2 and Comparative Example 1-1.

The following explanations on constituent elements are for embodiments (representative embodiments) of the invention, and the invention should not be construed as being limited to the embodiments.

In the process for bisphenol compound production of the invention, a phenol compound and a carbonyl compound are continuously fed to a reactor packed with an acidic catalyst to thereby produce a bisphenol compound.

(1) Phenol Compound

The bisphenol compound is produced by the condensation reaction of a phenol compound with a carbonyl compound. It is understood that the condensation reaction between a phenol compound and a carbonyl compound takes advantage of the strong ortho-para orientation, in particular, para orientation, of a phenolic hydroxyl group. It is therefore preferred that the phenol compound to be used should have no substituent in the ortho positions or in the para position. In particular, in view of the fact that the bisphenol compound to be obtained as a condensation reaction product preferably is a 4,4'-bisphenol compound from the standpoint of uses thereof, it is preferred to use a phenol compound having no substituent in the para position.

In the case where the phenol compound has a substituent group, this substituent group can be any desired substituent group according to the intended use and properties of the bisphenol compound to be obtained, unless the substituent group inhibits the ortho-para orientation of the phenolic hydroxyl group and causes steric hindrance to the site where condensation with the carbonyl compound occurs. Typical examples of the substituent group include lower alkyl groups having 1-4 carbon atoms. With respect to phenol compounds substituted with halogen atoms, such as fluorine, chlorine, and bromine atoms, in place of such substituent groups, compounds substituted in the same positions can be used. The phenol compound may have one substituent or may have a plurality of substituents.

Examples of the phenol compound include phenol (unsubstituted phenol), o-cresol, m-cresol, 2,5-xylenol, 2,6-xylenol, 2,3,6-trimethylphenol, 2,6-di-tert-butylphenol, o-chlorophenol, m-chlorophenol, 2,5-dichlorophenol, and 2,6-dichlorophenol. Especially preferred of these is phenol.

(2) Carbonyl Compound

The carbonyl compound is not particularly limited. Examples thereof include ketones having about 3-10 carbon atoms, such as acetone, methyl ethyl ketone, diethyl ketone, methyl isobutyl ketone, cyclohexanone, and acetophenone, and aldehydes having about 1-6 carbon atoms, such as formaldehyde, acetaldehyde, propionaldehyde, and butyraldehyde. Preferred of these is acetone. Use of phenol as the phenol compound and acetone as the carbonyl compound is especially preferred because bisphenol A, which is useful as a starting material for polycarbonate resins, etc., can be obtained in this case.

The molar ratio between the phenol compound and carbonyl compound to be used as starting materials for condensation reaction is as follows. The amount of the phenol compound per mole of the carbonyl compound is generally 2 mol or more, preferably 4 mol or more, and is generally 40 mol or less, preferably 30 mol or less. In the case where the phenol compound is used in too small an amount, by-products tend to be formed in an increased amount. On the other hand, even when the phenol compound is used in an excessively large amount, the effect thereof changes little. Such too large phenol compound amounts tend to be disadvantageous, rather than advantageous, from the standpoint of profitability because the amount of the phenol compound which must be recovered and reused increases.

(3) Acidic Catalyst (3-1) Sulfonic-Acid-Form Cation-Exchange Resin Catalyst

A sulfonic-acid-form cation-exchange resin catalyst in which part of the sulfo groups have been modified with at least any one of 2-pyridylalkanethiol compounds and 3-pyridylalkanethiol compounds is used as the acidic catalyst in the invention.

The sulfonic-acid-form cation-exchange resin to be subjected to the modification is a resin obtained by introducing sulfo groups into a styrene-based copolymer obtained by the copolymerization reaction of polymerizable monomers including a styrene monomer and a crosslinking monomer.

The term styrene monomer herein means a monomer which is either styrene or a styrene derivative in which the benzene ring or vinyl group of the styrene has any desired substituent(s) so long as the function of the ion-exchange resin is not impaired thereby. However, the styrene monomer may be a macromonomer constituted of any of polymers, e.g., a polyester, polycarbonate, polyamide, polyolefin, poly ((meth)acrylic ester), polyether, and polystyrene, and the macromonomer having a styryl structure at an end of oligomer. The term "(meth)acrylic" herein means "acrylic" and "methacrylic". The same applies to the term "(meth)acryloyl", which will be given later.

Preferred examples of the styrene monomer include monomers represented by the following formula (I).

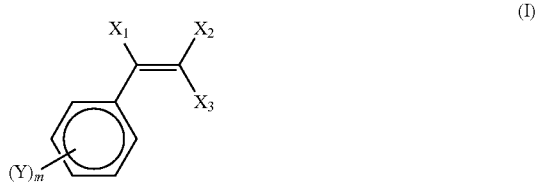

In formula (I), $X_1$, $X_2$, and $X_3$ represent any one of a hydrogen atom, an alkyl group, an aryl group, an alkoxy group, a halogen atom, an alkylsilyloxy group, a nitro group, and a nitrile group. Y represents a hydrogen atom, an amino group, an alkylamino group, an alkyl group, an alkenyl group, an alkynyl group, a halogen atom, a haloalkyl group, an aryl group, e.g., phenyl or naphthyl, an aralkyl group, e.g., benzyl, an alkoxyalkyl group, a nitro group, an alkanoyl group, an aroyl group, e.g., benzoyl, an alkoxycarbonyl group, an allylalkoxycarbonyl group, an alkoxy group, a haloalkoxy group, an allyloxy group, an aralkyloxy group, an alkoxyalkyloxy group, an alkanoyloxy group, an alkoxycarbonyloxy group, an aralkyloxycarbonyloxy group, or an alkylsilyloxy group.

Symbol m is an integer of 1 to 5, and $X_1$, $X_2$, and $X_3$ may be the same or different. In the case where m is 2 or larger, the plurality of Ys may be the same or different.

Specific examples of the styrene monomer include styrene, styrenes in which the benzene ring has been substituted with an alkyl group having 1-4 carbon atoms or with a halogen atom, such as o-methylstyrene, m-methylstyrene, p-methylstyrene, o-ethylstyrene, m-ethylstyrene, p-ethylstyrene, fluorostyrene, chlorostyrene, and bromostyrene, and styrenes in which the vinyl group has been substituted with an alkyl group having 1-4 carbon atoms or with a halogen atom, such as α-methylstyrene, α-fluorostyrene, and β-fluorostyrene.

One of these styrene monomers may be used alone, or a mixture of two or more thereof may be used.

Most preferred of these styrene monomers is styrene.

On the other hand, the crosslinking monomer is a compound having, in the molecule, two or more carbon-carbon double bonds copolymerizable with the styrene monomer. Examples thereof include polyvinylbenzenes such as divinylbenzene and trivinylbenzene, alkyldivinylbenzenes such as divinyltoluene, and aromatic divinyl compounds having a structure including two or more benzene rings bonded either directly or through a linking group, e.g., an alkylene group or a styrylene group, such as bis(vinylphenyl), bis(vinylphenyl) methane, bis(vinylphenyl)ethane, bis(vinylphenyl)propane, and bis(4-vinylphenyl)sulfone. The crosslinking monomer may be a macromonomer constituted of any of polymers, e.g., a polyester, polycarbonate, polyamide, polyolefin, poly ((meth)acrylic ester), polyether, and polystyrene, and the macromonomer having a polymerizable carbon-carbon double bond, such as a styryl structure or a (meth)acrylic structure, at each of both ends of oligomer.

One of these crosslinking monomers may be used alone, or a mixture of two or more thereof may be used. Preferred of those crosslinking monomers is divinylbenzene. Some divinylbenzene products contain a large amount of ethylvinylbenzene (ethylstyrene) which was formed as a by-product during production. In the invention, such divinylbenzene can also be used.

Although the polymerizable monomers to be used for producing a styrene-based copolymer include the styrene monomer and crosslinking monomer described above, other monomers copolymerizable with these monomers may be further contained besides these monomers according to need. Examples of such copolymerizable monomers (hereinafter often referred to as "third monomer") include: vinyl monomers having a polycyclic aromatic framework, such as naphthalenes, e.g., vinylnaphthalene, anthracenes, e.g., vinylanthracene, and vinylphenanthrene; (meth)acrylic esters such as methyl acrylate, ethyl acrylate, methyl methacrylate, and ethyl methacrylate; diene hydrocarbon compounds such as butadiene and isoprene; α-olefins such as 1-pentene and 1-hexene; and (meth)acrylonitrile. One of these may be used alone, or a mixture of two or more thereof may be used.

Use of such a third monomer produces the effect of enhancing oxidation resistance, etc. In this case, however, the amount of the third monomer to be used is generally 50% by mole or less, preferably 20% by mole or less, especially preferably 10% by mole or less, based on the styrene monomer. In the case where the third monomer is used in too large an amount, the resultant copolymer is reduced in the amount of sulfo groups capable of being introduced into the copolymer per unit weight thereof. There are hence the cases where the desired catalytic activity is not obtained.

The styrene-based copolymer obtained by polymerizing the polymerizable monomers including a styrene monomer and a crosslinking monomer has a degree of crosslinking which is preferably 1% or higher, more preferably 2% or higher, and is preferably 40% or less, more preferably 8% or less, especially preferably 5% or less. The term degree of crosslinking herein means the concentration by weight of the crosslinking monomer in the polymerizable monomers to be subjected to polymerization. This definition is the same as that used in this field.

In the case where the degree of crosslinking thereof is too low, it is difficult to make the resultant cation-exchange resin retain strength. When this cation-exchange resin is subjected, before being used in reaction as a catalyst for bisphenol compound production, to conditioning in which the resin is contacted with a phenol compound, a phenol compound/water mixed solvent, or the like, the resin suffers breakage or the like due to the expansion and contraction caused by the conditioning. Too low degrees of crosslinking are hence undesirable. On the other hand, in the case where the degree of crosslinking thereof is too high, the resultant copolymer particles are less apt to swell and, hence, diffusion resistance within the copolymer particles is apt to arise, resulting in a considerable decrease in catalytic activity. Too high degrees of crosslinking are hence undesirable.

The copolymerization reaction of the polymerizable monomers including a styrene monomer and a crosslinking monomer can be conducted using a radical polymerization initiator on the basis of a known technique.

As the radical polymerization initiator, use may be made of one or more members selected from benzoyl peroxide, lauroyl peroxide, tert-butyl hydroperoxide, azobisisobutyronitrile, and the like. Usually, the radical polymerization initiator is used in an amount of 0.05% by weight to 5% by weight based on the weight of the polymerizable monomers (weight of all monomers).

Polymerization modes are not particularly limited, and the polymerizable monomers can be polymerized in any of various modes such as, for example, solution polymerization, emulsion polymerization, and suspension polymerization. Classification with screens or the like can be conducted according to need.

The polymerization temperature in the copolymerization reaction is generally room temperature (about 18-25° C.) or higher, preferably 40° C. or higher, more preferably 70° C. or higher, and is generally 250° C. or lower, preferably 150° C. or lower, even more preferably 140° C. or lower. In the case where the polymerization temperature is too high, depolymerization concurs, resulting in a reduced, rather than increased, degree of completion of polymerization. In the case where the polymerization temperature is too low, the degree of completion of polymerization is insufficient.

With respect to polymerization atmosphere, the copolymerization reaction can be conducted in air or an inert gas. As the inert gas, use can be made of nitrogen, carbon dioxide, argon, or the like.

Methods for introducing sulfo groups (sulfonation) into the styrene-based copolymer obtained by the copolymerization reaction are not particularly limited, and the sulfonation can be conducted by an ordinary method.

For example, the sulfonation can be accomplished by reacting the copolymer with a sulfonating agent, e.g., sulfuric acid, chlorosulfonic acid, or fuming sulfuric acid, in the absence of any organic solvent or in the presence of an organic solvent such as benzene, toluene, xylene, nitrobenzene, chlorobenzene, tetrachloromethane, dichloroethane, trichloroethylene, or propylene dichloride. One organic solvent may be used alone, or a mixture of two or more organic solvents may be used. One sulfonating agent may be used alone, or a mixture of two or more sulfonating agents may be used.

This reaction may be conducted at a temperature of about 0-150° C., and the temperature is suitably selected according to the sulfonating agent and the organic solvent used.

The sulfonated copolymer is washed and separated by isolation, etc. in an ordinary manner to thereby obtain a sulfonic-acid-form, strongly acidic cation-exchange resin.

In the invention, the exchange capacity (amount of sulfo groups) of the strongly acidic cation-exchange resin is generally 0.5 meq/mL or more, preferably 1.0 meq/mL or more, and is generally 3.0 meq/mL or less, preferably 2.0 meq/mL or less, in terms of exchange capacity per unit volume of the wet-state resin. In the case of the dry-state resin, the exchange capacity thereof is generally 1.0 meq/g or more, preferably 2.0 meq/g or more, and is generally 6.0 meq/g or less, preferably 5.5 meq/g or less, per unit weight. In the case of the wet state obtained by removing adherent water from the wet-state resin, the exchange capacity thereof is generally 0.5 meq/g or more, preferably 1.0 meq/g or more, and is generally 3.0 meq/g or less, preferably 2.0 meq/g or less. In the case where the cation-exchange resin has too low an exchange capacity, the catalytic activity thereof is insufficient. On the other hand, a cation-exchange resin having an excessively high exchange capacity is difficult to produce.

The exchange capacity of a strongly acidic cation-exchange resin can be determined, for example, by the method described in "*Daiya Ion, Ion-k$\bar{o}$kan Jushi/G$\bar{o}$sei Ky $\bar{u}$chaku-zai Manuaru* 1" (Mitsubishi Chemical Corp. ed., 4th revised edition, published on Oct. 31, 2007, pp. 133-135) or by a method according to that method.

Examples of major types of the sulfonic-acid-form cation-exchange resin to be used here include a gel type and a porous type (porous type, highly porous type, or macro-porous type). In the case of use for the production of a bisphenol compound, the gel type is preferred from the standpoint of production cost. From the standpoint of ensuring the property of diffusing substances and the durability and strength of the resin, the porous type (porous type, highly porous type, or macro-porous type) is also preferred. Examples of the gel type include a simple gel type copolymer and an expanded network gel type copolymer, and either of these can be used. On the other hand, the porous type means a porous copolymer, and use can be made of a porous polymer having any desired values of surface area, porosity, average pore diameter, etc.

For obtaining a sulfonic-acid-form exchange resin of the gel type or the porous type, a conventionally known method can be used. For example, the resin can be produced in accordance with "*Ion-k$\bar{o}$kan Jushi, Sono Gijutsu To $\bar{O}$y$\bar{o}$*" (published by Organo Corp., revised edition, published on May 16, 1986, pp. 13-21).

With respect to the size of the sulfonic-acid-form cation-exchange resin, the average particle diameter thereof is generally 0.2 mm or more, preferably 0.4 mm or more, and is generally 2.0 mm or less, preferably 1.5 mm or less. Furthermore, the degree of monodispersity regarding particle size thereof is generally 1.6 or less, preferably 1.5 or less. The terms "average particle diameter" and "degree of monodispersity regarding particle diameter" used herein for resins are defined as values calculated by the method described in *Daiya Ion Manuaru* 1 (Mitsubishi Chemical Corp. ed., 4th edition, 2007, pp. 140-142).

(3-2) 2-Pyridylalkanethiol Compounds and 3-Pyridylalkanethiol Compounds

The 2-pyridylalkanethiol compounds in the invention are compounds in which the pyridine ring has been substituted, in the 2-position, with a mercaptoalkyl group or with a thioalkyl group in which the thiol moiety has been protected.

The pyridine ring and alkyl chain of each of the 2-pyridylalkanethiol compounds may have been substituted with any desired substituent group(s) or atom(s). The protective group in the thiol moiety is not particularly limited so long as the group can protect the sulfur atom. The thiol moiety can be protected by using the protective groups and methods for protection which are described in *Green's Protective Groups in Organic Synthesis*, Fourth Edition, Wiley (2007). Examples of the protected compounds include a thioether form obtained by protection with an aliphatic protective group which generates a stable carbocation, such as tertbutyl, a thioester form obtained by protection with a protective acyl group such as acetyl, a thiocarbonate form obtained by protection with a protective carbonate group, a benzyl thioether form obtained by protection with a protective benzyl group, and a dithioacetal form obtained by protection with a ketone or an aldehyde.

Preferred of these 2-pyridylalkanethiol compounds are compounds represented by the following general formula (II).

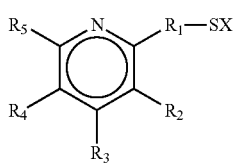

(II)

In general formula (II), $R_1$ represents a linear or branched alkylene group having 1-10 carbon atoms, and the alkylene group may have been partly substituted with one or more halogen atoms. $R_2$ to $R_5$ each independently represent a hydrogen atom, a linear or branched alkyl group having 1-10 carbon atoms, or a halogen atom. X represents a hydrogen atom, an alkyl group, an acyl group, a carbonate group, a benzyl group, or an acetal group.

Examples of the linear or branched alkylene group having 1-10 carbon atoms which is represented by $R_1$ include methylene, ethylene, trimethylene, and tetramethylene. Examples of the alkyl groups represented by $R_2$ to $R_5$ and X include methyl, ethyl, propyl, and butyl. Examples of the halogen atoms bonded as substituents to the alkylene group and of the halogen atoms represented by $R_2$ to $R_5$ include chlorine and bromine atoms. Examples of the acyl group represented by X include acetyl and ethylcarbonyl. Examples of the carbonate group include methoxycarbonyl and ethoxycarbonyl.

Specific examples of the 2-pyridylalkanethiol compounds represented by structural formula (II) in which $R_1$ is an alkylene group and $R_2$ to $R_5$ and X each are H include: 2-pyridylmethanethiol; 2-pyridylethanethiols such as 2-(2'-pyridyl)ethanethiol and 1-(2'-pyridyl)ethanethiol; 2-pyridylpropanethiols such as 3-(2'-pyridyl)propanethiol and 2-(2'-pyridyl)propanethiol; 2-pyridylbutanethiols such as 4-(2'-pyridyl)butanethiol, 3-(2'-pyridyl)butanethiol, and 2-(2'-pyridyl)butanethiol; and halogen-substituted thiols such as 2-chloro-2-(2'-pyridyl)ethanethiol and 2-bromo-2-(2'-pyridyl)ethanethiol. Preferred of these are 2-pyridylethanethiols. Especially preferred of these is 2-(2'-pyridyl)ethanethiol, which is ethanethiol having a 2-pyridyl group bonded thereto in the 2-position.

Meanwhile, the 3-pyridylalkanethiol compounds in the invention are compounds in which the pyridine ring has been substituted, in the 3-position, with a mercaptoalkyl group or with a thioalkyl group in which the thiol moiety has been protected. The pyridine ring and alkyl chain of each of the 3-pyridylalkanethiol compounds may have been substituted with any desired substituent group(s) or atom(s). Examples of protective groups for the thiol moiety and of methods for protection include the same protective groups and protection methods as those explained above with regard to the 2-pyridylalkanethiol compounds.

Preferred 3-pyridylalkanethiol compounds are compounds represented by the following general formula (III).

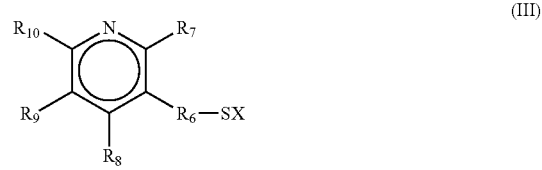

(III)

In general formula (III), $R_6$ represents a linear or branched alkylene group having 1-10 carbon atoms, and the alkylene group may have been partly substituted with one or more halogen atoms. $R_7$ to $R_{10}$ each independently represent a hydrogen atom, a linear or branched alkyl group having 1-10 carbon atoms, or a halogen atom. X represents a hydrogen atom, an alkyl group, an acyl group, a carbonate group, a benzyl group, or an acetal group.

Examples of $R_6$ in general formula (III) include the same groups as those shown as examples of $R_1$ contained in general formula (II). Examples of $R_7$ to $R_{10}$ in general formula (III) include the same groups and atoms as those shown above as examples of $R_2$ to $R_5$ contained in general formula (II).

Specific examples of the 3-pyridylalkanethiol compounds represented by structural formula (III) in which $R_6$ is an alkylene group and $R_7$ to $R_{10}$ and X each are H include: 3-pyridylmethanethiol; 3-pyridylethanethiols such as 2-(3'-pyridyl)ethanethiol and 1-(3'-pyridyl)ethanethiol; 3-pyridylpropanethiols such as 3-(3'-pyridyl)propanethiol and 2-(3'-pyridyl)propanethiol; 3-pyridylbutanethiols such as 4-(3'-pyridyl)butanethiol, 3-(3'-pyridyl)butanethiol, and 2-(3'-pyridyl)butanethiol; and halogen-substituted thiols such as 2-chloro-2-(3'-pyridyl)ethanethiol and 2-bromo-2-(3'-pyridyl)ethanethiol. Preferred of these are 3-pyridylethanethiols. Especially preferred of these is 2-(3'-pyridyl)ethanethiol, which is ethanethiol having a 3-pyridyl group bonded thereto in the 2-position.

The sulfonic-acid-form cation-exchange resin according to the invention may be a sulfonic-acid-form cation-exchange resin in which part of the sulfo groups have been modified with any one compound selected from 2-pyridylalkanethiol compounds and 3-pyridylalkanethiol compounds or may be a sulfonic-acid-form cation-exchange resin in which part of the sulfo groups have been modified with both a 2-pyridylalkanethiol compound and a 3-pyridylalkanethiol compound. One or more 2-pyridylalkanethiol compounds may be used for the modification, and one or more 3-pyridylalkanethiol compounds may be used for the modification.

However, from the standpoints of ease of catalyst modification and catalytic activity, it is preferred that part of the sulfo groups of the sulfonic-acid-form cation-exchange resin should have been modified with any one of 2-pyridylalkanethiol compounds and 3-pyridylalkanethiol compounds. It is especially preferred that part of the sulfo groups should have been modified with a 2-pyridylalkanethiol compound.

By modifying part of the sulfo groups of a sulfonic-acid-form cation-exchange resin with at least any one of 2-pyridylalkanethiol compounds and 3-pyridylalkanethiol compounds, the catalyst is inhibited from deteriorating and is rendered usable while attaining a high conversion over a long period.

When 4-pyridylalkanethiol compounds are compared with 2-pyridylalkanethiol compounds, these two kinds of compounds are thought to be substantially equal in stability because the two kinds of compounds are mere isomers. Consequently, 4-pyridylalkanethiol compounds, which bring about high initial activity, have conventionally been investigated and used as an effective promoter. However, an investigation made lately revealed that 2-pyridylalkanethiol compounds are less apt to suffer the thermal alteration from thiol to sulfide. Since the reactions for producing bisphenols are exothermic reactions, the catalysts are continuously exposed to heat and, hence, the pyridylalkanethiols are gradually altered to sulfides to deteriorate the catalyst performance. However, because of the thermal resistance of 2-pyridylalkanethiol compounds, by modifying a sulfonic-acid-form cation-exchange resin with a 2-pyridylalkanethiol compound, this catalyst can be rendered usable while retaining a highly active state over a prolonged period.

Furthermore, the catalyst obtained by modifying a cation-exchange resin with a 2-pyridylalkanethiol compound can retain the activity thereof over a prolonged period even when phenol containing impurities in some degree is used, as in the case of using pure phenol containing substantially no impurities, as compared with catalysts obtained by modifying a cation-exchange resin with conventionally known modifiers such as aminoalkanethiol compounds represented by 2-aminoethanethiol and 4-pyridylalkanethiol compounds.

(3-3) Methods for Producing the 2-Pyridylalkanethiol Compounds

The 2-pyridylalkanethiol compounds to be used in the invention may be either commercial products or compounds produced in accordance with known methods represented by the methods described in, for example, JP-A-2002-003475, JP-A-2002-220373, and JP-A-2005-170820.

(3-3-1) Methods for Producing 2-Pyridylethanethiol

The 2-pyridylethanethiol to be used in the invention can be produced from 2-vinylpyridine and a sulfur-containing compound in accordance with ordinary methods.

Examples of the methods include: a method in which thiourea is used as a sulfur-containing compound to obtain an isothiuronium salt and the isothiuronium salt obtained is hydrolyzed; a method in which thioacetic acid is used as a sulfur-containing compound to obtain a pyridylethyl thioacetate; and a method in which hydrogen sulfide is used as a sulfur-containing compound to obtain the pyridylethanethiol.

The method in which thiourea is used as a sulfur-containing compound is explained below as a representative example.

First, 2-vinylpyridine is reacted with thiourea in the presence of an acid to obtain an isothiuronium salt represented by the following general formula (IV).

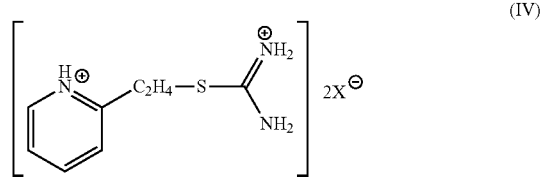

In general formula (IV), X⁻ is a residue of the acid used.

As the acid, use may be made of an organic acid such as p-toluenesulfonic acid, benzenesulfonic acid, or trifluoromethanesulfonic acid, a general inorganic acid such as sulfuric acid, hydrochloric acid, or nitric acid, or the like. Preferred of these from the standpoint of handleability are aromatic sulfonic acids such as p-toluenesulfonic acid and benzenesulfonic acid and sulfuric acid. Especially preferred is p-toluenesulfonic acid or sulfuric acid.

The acid is used at least in a stoichiometric amount based on the 2-vinylpyridine. However, since use of the acid in large excess results in the possibility of arousing side reactions, the acid is used in an amount of generally up to 4 equivalents, preferably up to 3 equivalents, to the 2-vinylpyridine. On the other hand, thiourea is used in a stoichiometric amount based on the 2-vinylpyridine or in a slightly larger amount. The amount thereof is generally up to 1.5 equivalents, preferably up to 1.3 equivalents, to the 2-vinylpyridine.

The reaction between 2-vinylpyridine and thiourea may be conducted in the following manner. An acid and thiourea are added to and dissolved in a reaction solvent, and 2-vinylpyridine is thereafter added dropwise to the solution. This reaction is preferably conducted in an inert gas atmosphere, e.g., nitrogen. It is preferred that the concentration of the acid in the liquid reaction mixture should be higher so long as the ease of reaction operation is not impaired. In the case of sulfuric acid, the concentration thereof is generally 5-50% by weight, preferably 20-40% by weight. The reaction temperature is generally 30-100° C., preferably 50-100° C. The reaction period is generally 1-10 hours.

Examples of the reaction solvent include organic solvents such as alcohols or aqueous solvents.

It is preferred that 2-vinylpyridine and thiourea should be reacted with each other in the presence of water and a hydrocarbon solvent. The hydrocarbon solvent to be used as a reaction solvent together with water may be any hydrocarbon solvent which is insoluble in water and is capable of undergoing phase separation from water. For example, aromatic hydrocarbons such as benzene, toluene, and xylene, halogenated hydrocarbons such as dichloroethane and carbon tetrachloride, and the like are used. One of these hydrocarbon solvents may be used alone, or a mixture of two or more thereof may be used. Toluene is suitable among these from the standpoint of solubility of the thiol compound.

The reaction between 2-vinylpyridine and thiourea which is conducted in the presence of the hydrocarbon solvent and water produces the effects of improving the yield of 2-pyridylethanethiol and preventing polymer formation. Although the mechanism by which these effects are produced has not been elucidated in detail, it is presumed that since the 2-vinylpyridine is diluted, the rate of polymerization decreases and polymer formation is inhibited, thereby producing the effects.

The amount of the hydrocarbon solvent to be used is preferably 0.5-10 times by volume, more preferably 1-3 times by volume, the amount of the 2-vinylpyridine. In the case where the hydrocarbon solvent is used in too small an amount, the effect of inhibiting polymer formation is low to pose problems such as a decrease in yield, adhesion of solid matter (polymer) to inner parts of the apparatus, clogging of the piping, etc. In the case where the hydrocarbon solvent is used in too large an amount, the amount of the liquid reaction mixture is increased and, hence, excessively large reaction equipment is necessary, resulting in the necessity of an enormous investment in the equipment. In addition, since it is necessary to remove the hydrocarbon solvent by distillation after the reaction, use of the hydrocarbon solvent in a large amount requires a distillation cost.

On the other hand, the amount of the water to be used is preferably 1-20 times by volume, more preferably 3-10 times by volume, the amount of the 2-vinylpyridine. In the case where water is used in too small an amount, the acid concentration increase and, hence, side reactions are apt to occur, resulting in problems such as a decrease in selectivity. In the case where water is used in too large an amount, the acid concentration decreases and, hence, the reaction between the 2-vinylpyridine and thiourea becomes considerably slow and side reactions including 2-vinylpyridine polymerization reaction are apt to occur, resulting in problems such as a decrease in yield. In addition, since the amount of the liquid reaction mixture is increased, excessively large reaction equipment is necessary, resulting in the necessity of an enormous investment in the equipment.

With respect to the ratio between the hydrocarbon solvent and water to be used, it is preferred that the volume ratio of hydrocarbon solvent/water should be in the range of 1/(1-10), in particular, 1/(2-5). When the amount of the water is more than the upper limit and the amount of the hydrocarbon solvent is less than the lower limit, then the effect of inhibiting polymer formation is reduced and, in particular, there are the cases where the effects of the invention are difficult to obtain. Conversely, when the amount of the hydrocarbon solvent is more than the upper limit and the amount of the water is less than the lower limit, then it is necessary to increase the amount of the liquid reaction mixture in order to ensure the necessary water amount. There are hence the cases where excessive reaction equipment is necessary, resulting in the necessity of an enormous investment in the equipment.

Methods for causing water and a hydrocarbon solvent to be present as a reaction solvent in the reaction system are not particularly limited. For example, use may be made of a method in which 2-vinylpyridine is mixed beforehand with a hydrocarbon solvent and this mixture is added to an aqueous acid solution in which thiourea has been dissolved. Alternatively, use may be made of a method in which a hydrocarbon solvent is added beforehand to an aqueous acid solution in which thiourea has been dissolved, and 2-vinylpyridine is added to the resultant oil/water two-phase mixture. Furthermore, use may be made of a method in which part of a hydrocarbon solvent is added beforehand to an aqueous acid solution in which thiourea has been dissolved, and a mixture of 2-vinylpyridine and the remainder of the hydrocarbon solvent is added to the resultant oil/water two-phase mixture.

Subsequently, after completion of the reaction for forming an isothiuronium salt, the isothiuronium salt obtained is hydrolyzed with an alkali to obtain 2-pyridylethanethiol, which is represented by the following general formula (V).

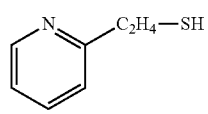
(V)

The hydrolysis reaction of the isothiuronium salt is specifically conducted by adding an alkali to the liquid reaction mixture, in which the isothiuronium salt has been yielded, and thereby rendering the liquid reaction mixture alkaline. Although a metal hydroxide such as sodium hydroxide can be used, it is preferred to use ammonia as the alkali. In the case where ammonia is used, the hydrolysis reaction proceeds as shown by the following scheme.

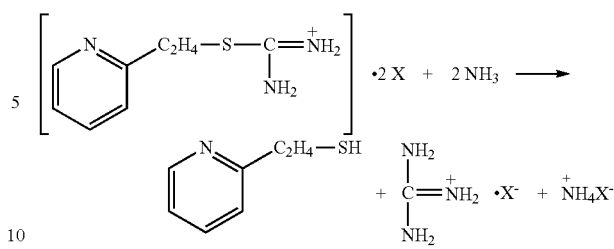

In the reaction scheme, $X^-$ has the same meaning as in general formula (IV).

The stoichiometric amount of the ammonia to be used is 2 times by mole the amount of the isothiuronium salt. However, ammonia is used usually in excess in order to cause the reaction to proceed sufficiently. Specifically, the amount of the ammonia to be used is generally 3-15 times by mole, preferably 3-5 times by mole, the amount of the 2-vinylpyridine used as a starting material, besides the amount necessary for neutralizing the acid used in the preceding step and present in the isothiuronium salt solution. Too large use amounts of ammonia generally result in a decrease in yield. This is presumed to be attributable to side reactions which the yielded 2-pyridylethanethiol undergoes. Although the ammonia is usually used in the form of ammonia water, which is easy to handle, the concentration thereof may be suitably determined while taking account of processability during the succeeding filtration and extraction steps. Usually, ammonia water having a concentration of about 5-28% by weight is used.

In this hydrolysis reaction, an organic solvent which serves as the extractant that will be described later may be added according to need to the liquid reaction mixture in which the isothiuronium salt has been yielded, in an amount of about 0.1 to 1 time the amount of the water phase to dilute the reaction mixture. This dilution produces the effect of further inhibiting polymer formation.

The hydrolysis reaction for converting the isothiuronium salt to 2-pyridylethanethiol is completed in 0.5-10 hours when conducted at a temperature of 30-70° C. with stirring. Although this hydrolysis reaction proceeds even at room temperature, the rate of this reaction is low. On the other hand, when the reaction is conducted at high temperatures, side reactions tend to occur, resulting in a reduced yield.

In the case where an aromatic sulfonic acid was used as the acid, the liquid reaction mixture after completion of the reaction is cooled to about 10° C. to precipitate the guanidinium salt formed as a by-product. An extractant such as toluene is further added, and the resultant mixture is filtered to remove insoluble matter. The cake is washed with an extractant, and the washings are added to the filtrate. Subsequently, the filtrate is subjected to liquid separation, and the extractant is recovered.

On the other hand, in the case where an inorganic acid such as sulfuric acid was used as the acid, cooling does not result in precipitation of a guanidinium salt. Consequently, the filtration may be omitted, and the liquid reaction mixture may be directly subjected to an extraction operation using an organic solvent.

In either case, the water phase is extracted with an extractant and the resultant extractant phase is added to the extractant phase obtained previously. From this extractant phase obtained by the addition, the extractant is distilled away.

Thereafter, the residual liquid is distilled under vacuum. Thus, 2-pyridylethanethiol as the target substance can be obtained.

In the case where 2-pyridylethanethiol obtained in the absence of any hydrocarbon solvent, not in accordance with the invention, is used as such to modify a sulfonic-acid-form cation-exchange resin to be used as an acidic catalyst, there is a possibility that the obtained polymers might adhere to the surface of the sulfonic-acid-form cation-exchange resin during the reaction, resulting in insufficient catalyst performance.

In the invention, when 2-vinylpyridine is to be reacted with a sulfur-containing compound to obtain 2-pyridylethanethiol, it is preferred to use 2-vinylpyridine in which the content of 2-vinylpyridine-containing polymers that are the dimer and higher polymers is 2% by weight or less. Using such 2-vinylpyridine having a low polymer content, 2-pyridylethanethiol can be produced in high yield without arousing the problem of scale deposition.

In contrast, in the case where 2-pyridylethanethiol obtained using 2-vinylpyridine in which the content of 2-vinylpyridine-containing polymers that are the dimer and higher polymers was higher than 2% by weight, not in accordance with the invention, is used as such to modify a sulfonic-acid-form cation-exchange resin to be used as an acidic catalyst, there is a possibility that the residual polymers might adhere to the surface of the sulfonic-acid-form cation-exchange resin, resulting in insufficient catalyst performance.

(3-3-2) Method for Producing 2-Vinylpyridine

It is preferred in the invention that the 2-vinylpyridine to be used as a starting material for 2-pyridylethanethiol should be produced by the following production method.

2-Vinylpyridine is apt to polymerize during the synthesis thereof and during subsequent storage thereof because of the positions of the vinyl group and the nitrogen atom of the pyridine ring, and is hence apt to have a higher polymer content. Although 2-vinylpyridine has the property of readily forming polymers, the effects of the invention are effectively exhibited by removing the polymers contained in the 2-vinylpyridine to 2% by weight or less.

The term "polymers contained in 2-vinylpyridine" as used in the invention means the dimer and higher polymers which were formed during synthesis or during the subsequent storage of the 2-vinylpyridine product through polymerization of the 2-vinylpyridine with itself or with polymerizable impurities.

In the case where the amount of polymers contained in the 2-vinylpyridine to be used as a starting material for 2-pyridylethanethiol is more than 2% by weight, production of 2-pyridylethanethiol therefrom result not only in a decrease in output per unit feed amount but also in enhanced formation of solid matter. This enhanced solid-matter formation arouses a trouble concerning clogging of the piping and necessitates cleaning for removing the solid matter adherent to inner parts of the apparatus, etc., resulting in a considerable decrease in production efficiency.

So long as the 2-vinylpyridine has a polymer content of 2% by weight or less, not only 2-pyridylethanethiol can be obtained therefrom in high yield but also deposition of solid matter is reduced. Consequently, clogging of the piping is less apt to occur, and the frequency of cleaning for removing the solid matter adherent to inner parts of the apparatus can be reduced or the cleaning can be rendered unnecessary. A high production efficiency can hence be maintained.

The smaller the amount of polymers contained in the 2-vinylpyridine, the more the 2-vinylpyridine is preferred. The content thereof is more preferably 1.0% by weight or less, more preferably 0.5% by weight or less. It is, however, noted that for removing the polymers to an extremely low concentration, it is necessary to conduct to a high degree the purification operation which will be described later and it is also necessary to conduct purification by distillation again just before use. Namely, to attain an exceedingly low polymer concentration is highly costly because of the purification and distillation. Alternatively, it is necessary to use a large amount of a polymerization inhibitor or store the 2-vinylpyridine at an exceedingly low temperature in order to inhibit polymer formation during storage, resulting in an increase in the cost of storage and transportation. In addition, it is difficult to obtain effects which compensate for the cost increase. It is therefore preferred that the lower limit of the content of polymers contained in the 2-vinylpyridine should be 100 weight ppm.

With respect to methods for determining the amount of polymers contained in 2-vinylpyridine, the amount of low-molecular polymers such as the dimer, trimer, and the like among those polymers can be directly determined by NMR (nuclear magnetic resonance), GC (gas chromatography), LC (liquid chromatography), and the like.

On the other hand, examples of methods for determining the amount of high-molecular polymers, specifically, the tetramer and higher polymers, include a method in which the 2-vinylpyridine is examined by GPC (gel permeation chromatography) to detect peaks with a UV (ultraviolet) detector, RI (differential refractometer) detector, or the like and the content of the high-molecular polymers is calculated from the peaks. Examples thereof further include a method in which the polymers are separated by the reprecipitation method while utilizing a difference in solubility in an organic solvent between the monomer and the polymers and the weight of the polymers separated and recovered is measured to thereby determine the content of the polymers.

The molecular weights of those high-molecular polymers can be calculated from the peaks obtained by GPC, using standard polystyrene samples.

The polymers contained in 2-vinylpyridine directly affect the purity of the 2-vinylpyridine, and are a cause which brings about a decrease in the yield of 2-pyridylethanethiol. Of these polymers, high-molecular polymers having a molecular weight of, in particular, 2,000 or higher remain as such within the 2-pyridylethanethiol production system or further polymerize or react with other substances within the system to form solid matter which does not dissolve in the reaction solvent. Consequently, the 2-vinylpyridine to be used in the invention is 2-vinylpyridine in which the content of high-molecular polymers having a molecular weight of, in particular, 2,000 or higher, among the 2-vinylpyridine-containing polymers that are the dimer and higher polymers, is preferably 1.0% by weight or less, more preferably 0.5% by weight or less.

It is therefore preferred to use 2-vinylpyridine which has a polymer content, as determined by the GPC method that will be described later in the section Examples, of 1.0% by weight or less, in particular, 0.5% by weight or less, and a polymer content as determined by the reprecipitation method of 1.0% by weight or less, in particular, 0.5% by weight or less. The lower limit of the content of these high-molecular polymers also is preferably 100 weight ppm for the same reasons as in the case of the polymers described above.

Methods for reducing the amount of polymers contained in the 2-vinylpyridine to 2% by weight or less are not particularly limited. Usually, a purification technique based on distillation is employed. For example, a vacuum distillation apparatus is used to purify the 2-vinylpyridine. Specifically, a distillation column, preferably a packed column, that has an equivalent number of plates of generally 1 or more, preferably 2-10, may be used to conduct distillation while regulating pressure and other conditions so as to result in a column top temperature of preferably 30-150° C.

It is preferred to add a polymerization inhibitor, such as tert-butylpyrocatechol or hydroquinone, to the purified 2-vinylpyridine in an amount of about 100-1,000 weight ppm and store this 2-vinylpyridine at a low temperature of about −5° C. or below, for example, −5° C. to −40° C., in order to prevent polymer formation during storage.

(3-3-3) Sulfur-Containing Compound

In the invention, the kind of the sulfur-containing compound as a starting material for 2-pyridylethanethiol is not particularly limited, and any sulfur-containing compound which reacts with 2-vinylpyridine and thereby yield 2-pyridylethanethiol may be used. Examples of the sulfur-containing compound include thiourea, thioacetic acid, hydrogen sulfide, and sodium sulfide. Preferred is thiourea or thioacetic acid. Especially preferred of these is thiourea from the standpoints of handleability and reaction yield.

(3-4) Method for Producing 3-Pyridylalkanethiols

The 3-pyridylalkanethiols to be used in the invention can be synthesized by any desired method. For example, a 3-pyridylalkanethiol can be obtained by halogenating the terminal hydroxyl group of the corresponding 3-pyridylalkanol with a thionyl halide or the like and reacting the resultant alkyl halide derivative with an alkali metal thioacetate, thiourea, or the like.

Specifically, in the case where 3-pyridylacetic acid is used as a starting substance, the procedure is as follows. 3-Pyridylacetic acid is reacted with thionyl chloride and methanol to thereby convert the acid into a methyl ester, which is then reduced with sodium borohydride to thereby obtain 3-pyridylethanol. The 3-pyridylethanol obtained is reacted with thionyl chloride to thereby synthesize the corresponding chloride, and the chloride obtained is reacted with potassium thioacetate to thereby synthesize a thioester. The thioester obtained is reduced with lithium aluminum hydride. Thus, 3-pyridylethanethiol can be obtained.

(3-5) Methods for Producing the Acidic Catalyst (3-5-1) Modification of Sulfonic-Acid-Form Cation-Exchange Resin with at Least any One of 2-Pyridylalkanethiol Compounds and 3-Pyridylalkanethiol Compounds The acidic catalyst to be used in the invention can be obtained by modifying a sulfonic-acid-form cation-exchange resin with at least any one of 2-pyridylalkanethiol compounds and 3-pyridylalkanethiol compounds.

The ratio of modification of the sulfonic-acid-form cation-exchange resin with at least any one of 2-pyridylalkanethiol compounds and 3-pyridylalkanethiol compounds is such that preferably 3% by mole or more, more preferably 5% by mole or more, of all sulfo groups of the sulfonic-acid-form cation-exchange resin are modified. The ratio of modification thereof is preferably 70% by mole or less, more preferably 50% by mole or less, especially preferably 30% by mole or less. Thus, the effect of making the at least any one of 2-pyridylalkanethiol compounds and 3-pyridylalkanethiol compounds function as a promoter can be maximized while avoiding the decrease in activity which is caused by a decrease in the amount of sulfo groups necessary for the reaction.

In the case where the ratio of modification of the sulfonic-acid-form cation-exchange resin with at least any one of 2-pyridylalkanethiol compounds and 3-pyridylalkanethiol compounds is too low, the promoter tends to be reduced in the effect of improving reactivity. Namely, there is a tendency that the effect of enabling the catalyst to retain the activity thereof over a prolonged period becomes insufficient. In the case where the ratio of modification thereof is too high, the amount of sulfo groups which take part in the reaction is reduced and, hence, reactivity tends to decrease. In addition, too high ratios of modification mean that the thiol compound, which is costly, is used in a large amount.

In the case where sulfo groups of a sulfonic-acid-form cation-exchange resin have been modified with both a 2-pyridylalkanethiol compound and a 3-pyridylalkanethiol compound, the proportion between the 2-pyridylalkanethiol compound and the 3-pyridylalkanethiol compound is not particularly limited. It is, however, noted that it is preferred that the sulfo groups have been modified with either of the two.

For modifying a sulfonic-acid-form cation-exchange resin with at least any one of 2-pyridylalkanethiol compounds and 3-pyridylalkanethiol compounds, a known method may be used. For example, the modification is conducted in the following manner according to the method shown in, for example, JP-A-11-246458. At least any one of 2-pyridylalkanethiol compounds and 3-pyridylalkanethiol compounds is dissolved in a solvent, e.g., water, an alcohol, a ketone, an ether, or phenol, and this solution is dropped into the sulfonic-acid-form cation-exchange resin dispersed in such a solvent. Alternatively, at least any one of 2-pyridylalkanethiol compounds and 3-pyridylalkanethiol compounds which has not been diluted with a solvent is directly dropped into the sulfonic-acid-form cation-exchange resin dispersed in that solvent. The at least one thiol compound is thus mixed with the cation-exchange resin, and the mixture is stirred to thereby accomplished the modification. In this method, part of the sulfo groups of the sulfonic-acid-form cation-exchange resin react (are neutralized) with the thiol compound and form ionic bonds, and are thereby modified.

In the case where the sulfonic-acid-form strong cation-exchange resin to be used as an acidic catalyst for bisphenol compound production in the invention contains moisture remaining therein, this moisture constitutes a factor which inhibits the reaction. It is therefore preferred that the cation-exchange resin, before being used in the reaction, should be brought into contact with the phenol compound to be used as a starting material and the moisture within the ion-exchange resin be thereby removed beforehand. This treatment shortens the induction period necessary for initiating the reaction, and the cation-exchange resin can be rapidly rendered usable for the reaction.

(3-5-2) Modification of Sulfonic-Acid-Form Cation-Exchange Resin with Compound Obtained by Protecting Thiol Group of at Least any One of 2-Pyridylalkanethiol Compounds and 3-Pyridylalkanethiol Compounds with Acyl Group The acidic catalyst to be used in the invention may be obtained through the following steps.

(I) A modification step in which a sulfonic-acid-form cation-exchange resin is modified using a compound obtained by protecting the thiol group of at least any one of 2-pyridylalkanethiol compounds and 3-pyridylalkanethiol compounds with an acyl group.

(II) A hydrolysis step in which the thioester moiety of the compound obtained by protecting the thiol group of at least any one of 2-pyridylalkanethiol compounds and 3-pyridylalkanethiol compounds with an acyl group is hydrolyzed at a temperature of 40° C. to 100° C. during the modification of step (I) and/or after the modification of step (I).

Each step is explained below.

(I) Modification Step in which Sulfonic-Acid-Form Cation-Exchange Resin is Modified Using Compound Obtained by Protecting Thiol Group of at Least any One of 2-Pyridylalkanethiol Compounds and 3-Pyridylalkanethiol Compounds with Acyl Group The 2-pyridylalkanethiol compounds and the 3-pyridylalkanethiol compounds are not particularly limited, so long as these compounds form ionic bonds with sulfo groups of the cation-exchange resin which will be described above. Examples thereof include 3-pyridylmethanethiol, 2-pyridylethanethiol, and 3-pyridylethanethiol. In particular, 2-pyridylethanethiol and 3-pyridylethanethiol are preferred because these compounds bring about improvements in conversion and selectivity and inhibit the acidic catalyst from decreasing in activity when used over a prolonged period. One of those compounds may be used alone, or a mixture of two or more thereof may be used.

It is preferred that the 2-pyridylalkanethiol compounds and 3-pyridylalkanethiol compounds to be used should be high-purity compounds which have been purified. However, these compounds may contain impurities, e.g., disulfides, so long as the impurities do not considerably inhibit the reaction when the modified strongly acidic cation-exchange resin is used as a catalyst.

Examples of the acyl group for protecting the thiol group include groups having the following formula (VI).

$$R_a\text{—CO—} \qquad (VI)$$

Examples of $R_a$ in formula (VI) include linear or branched hydrocarbon groups having 1-20 carbon atoms, such as methyl, ethyl, n-propyl, isopropyl, n-butyl, isobutyl, and tert-butyl, and a hydrogen atom. Aromatic groups, e.g., phenyl, halogen atoms, other various functional groups, and the like may have been further bonded to these hydrocarbon groups.

Of these, acetyl, in which $R_a$ is methyl, is especially preferred from the standpoints of ease of synthesis, etc. Elimination of the acetyl group by hydrolysis reaction yields acetic acid.

Namely, the compounds for use in the invention which have been obtained by protecting the thiol group of each of 2-pyridylalkanethiol compounds with an acyl group preferably are 2-pyridylethyl thioacetate. The compounds obtained by protecting the thiol group of each of 3-pyridylalkanethiol compounds with an acyl group preferably are 3-pyridylethyl thioacetate.

The compounds obtained by protecting the thiol groups of 2-pyridylalkanethiol compounds and 3-pyridylalkanethiol compounds with acyl groups can be synthesized by known methods. For example, the compounds can be synthesized by the method described in U.S. Pat. No. 2,607,776.

In general, protective groups bonded to the terminal sulfur atoms of 2-pyridylalkanethiol compounds and 3-pyridylalkanethiol compounds are intended to inhibit oxidation of the terminal sulfur atoms. Usually, unprotected thiol groups are readily oxidized into disulfides during storage or synthesis or under reaction conditions for modifying sulfonic-acid-form cation-exchange resins, etc., and this reduces the performance of the compounds as a promoter. Furthermore, the 2-pyridylalkanethiol compounds and 3-pyridylalkanethiol compounds in which the sulfur sites have been protected have a considerably reduced odor as compared with the 2-pyridylalkanethiol compounds and 3-pyridylalkanethiol compounds in which the sulfur sites are unprotected. The compound to be used in the invention which has been obtained by protecting the thiol group of at least any one of 2-pyridylalkanethiol compounds and 3-pyridylalkanethiol compounds with an acyl group not only has the same effect but also has an advantage that the acyl group can be readily hydrolyzed to thereby efficiently yield a thiol group, which is useful as a promoter.

The compound which has been obtained by protecting the thiol group of at least any one of 2-pyridylalkanethiol compounds and 3-pyridylalkanethiol compounds with an acyl group and which is to be used for modifying a sulfonic-acid-form cation-exchange resin in the invention may be a compound derived from one 2-pyridylalkanethiol compound or 3-pyridylalkanethiol compound, or may be compounds derived from two or more 2-pyridylalkanethiol compounds or 3-pyridylalkanethiol compounds. With respect to the acyl group for protecting the thiol group also, use may be made of one kind of acyl group or two or more kinds of acyl groups.

The modification of the sulfonic-acid-form cation-exchange resin with the compound obtained by protecting the thiol group of at least any one of 2-pyridylalkanethiol compounds and 3-pyridylalkanethiol compounds with an acyl group may be accomplished by reacting the sulfonic-acid-form cation-exchange resin with the compound in the presence of a suitable organic solvent and/or an aqueous solvent. The reaction solvent to be used is not particularly limited so long as the solvent does not undergo an acid-base reaction with sulfo groups of the sulfonic-acid-form cation-exchange resin.

Preferred examples of solvents usable as the reaction solvent include water and highly polar organic solvents such as alcohols, ketones, ethers, and phenols. One of these solvents may be used alone, or a mixture of two or more thereof may be used. For the purpose of more evenly modify the cation-exchange resin, use may be made of a solvent in which acetic acid, monochloroacetic acid, trifluoroacetic acid, etc. have been dissolved. It is preferred to use a solvent prepared by dissolving these compounds in water.

Hydrolysis can be conducted simultaneously with the modification. It is therefore preferred to conduct the modification in the presence of water. For example, it is preferred to conduct the modification reaction in a mixed solvent composed of water and an organic solvent or in a water solvent.

The modification reaction temperature is not particularly limited so long as the temperature does not exceed the boiling point of the solvent used. However, when the temperature is too high, there are the cases where the compound for modification obtained by protecting the thiol group of at least any one of 2-pyridylalkanethiol compounds and 3-pyridylalkanethiol compounds with an acyl group reacts and causes side reactions, etc., resulting in a decrease in yield. It is therefore preferred to conduct the modification at ordinary temperature, which requires no heating or cooling operation. In the case where hydrolysis is conducted simultaneously with the modification, however, this modification is conducted at the hydrolysis temperature which will be described later.

The modification reaction can be carried out either batch-wise or continuously. However, the batch reaction is preferred because the apparatus and operation are simple. It is also preferred that the modification reaction should be conducted in an inert gas atmosphere, e.g., nitrogen, in order to prevent the at least any one of 2-pyridylalkanethiol compounds and 3-pyridylalkanethiol compounds from oxidatively deteriorating.

In the case of continuous reaction, examples of methods therefor include a method in which the sulfonic-acid-form cation-exchange resin is disposed as a fixed bed and a solution containing, dissolved therein, the modifier compound obtained by protecting the thiol group of at least any one of 2-pyridylalkanethiol compounds and 3-pyridylalkanethiol compounds with an acyl group is passed through the fixed bed. In this method, however, there are the cases where it is difficult to evenly modify the whole cation-exchange resin.

In the case of batch reaction, use may be made, for example, of a method in which the sulfonic-acid-form cation-exchange resin and a solvent constituted of water and/or an organic solvent are placed in a reactor and the modifier is further added. In this method, it is preferred that a reaction system constituted of a mixture of the sulfonic-acid-form cation-exchange resin, the compound obtained by protecting the thiol group of at least any one of 2-pyridylalkanethiol compounds and 3-pyridylalkanethiol compounds with an acyl group, and a solvent should be formed and the cation-exchange resin be modified while stirring the reaction system.

Especially when water is used as a solvent, the following effects are produced. Even when the compound serving as a modifier, which has been obtained by protecting the thiol group of at least any one of 2-pyridylalkanethiol compounds and 3-pyridylalkanethiol compounds with an acyl group, and the water are present as separate two phases, the modifier is dispersed as droplets in the water by stirring the mixture. The dispersed droplets gradually dissolve in the water, and the cation-exchange resin is evenly modified. Furthermore, this method is preferred because the carboxylic acid formed as a by-product of the hydrolysis dissolves in the water and can be easily removed.

The amount of the solvent to be used varies depending on the kind thereof. However, the amount thereof is preferably 0.5-100 times by weight, more preferably 1-10 times by weight, the amount of the sulfonic-acid-form cation-exchange resin. Use amounts of the solvent more than the upper limit are undesirable because the amount of waste liquid increases and this necessitates huge equipment. Too small amounts thereof are undesirable because there are the cases where it is difficult to evenly modify the sulfo groups.

Modification period differs between the case in which modification only is conducted and the case in which modification and hydrolysis are simultaneously conducted. In the case where modification only is conducted, the modification period is preferably 0.5-4 hours, more preferably 1-3 hours. In the case where modification and hydrolysis are simultaneously conducted, the modification period is preferably 0.5-6 hours, more preferably 1-4 hours. In the case where the reaction period is too short, the desired reaction does not proceed sufficiently. Even when the reaction period is excessively long, it cannot be expected that the reaction proceeds further and this reaction is not efficient.

The amount of the compound to be used for the modification, which has been obtained by protecting the thiol group of at least any one of 2-pyridylalkanethiol compounds and 3-pyridylalkanethiol compounds with an acyl group, is suitably determined according to the desired degree of modification.

(II) Hydrolysis Step in which Thioester Moiety of the Compound Obtained by Protecting Thiol Group of At Least any One of 2-Pyridylalkanethiol Compounds and 3-Pyridylalkanethiol Compounds with Acyl Group is Hydrolyzed at Temperature of 40° C. to 100° C. During Modification of Step (I) and/or after Modification of Step (I)

In step (II), the thioester moiety of the compound obtained by protecting the thiol group of at least any one of 2-pyridylalkanethiol compounds and 3-pyridylalkanethiol compounds with an acyl group is hydrolyzed in the presence of a solvent including water. Examples of usable solvents other than water include the solvents usable in the modification step. One of these solvents may be used alone, or a mixture of two or more thereof may be used. In the case where a mixed solvent composed of water and other solvent(s) is used as that solvent, this mixed solvent has a water content of preferably 1% by weight or higher, more preferably 10% by weight or higher, from the standpoint of ensuring the amount of water necessary for the hydrolysis. It is preferred that the hydrolysis should be conducted in a water solvent.

The amount of the solvent to be used varies depending on the kind thereof. However, the amount thereof is preferably 0.5-100 times by weight, more preferably 1-10 times by weight, the amount of the sulfonic-acid-form cation-exchange resin. Use amounts of the solvent more than the upper limit are undesirable because the amount of waste liquid increases and this necessitates huge equipment. Too small amounts thereof are undesirable because there are the cases where the hydrolysis (deprotection reaction of the thiol group) does not proceed sufficiently.

It is preferred that the hydrolysis of the thioester moiety in the compound obtained by protecting the thiol group of at least any one of 2-pyridylalkanethiol compounds and 3-pyridylalkanethiol compounds with an acyl group should be conducted at a temperature in the range of preferably 40-100° C., more preferably 50-95° C., even more preferably 60-90° C., most preferably 70-85° C.

In the case where the temperature is lower than said lower limit, the hydrolysis requires a long period or a large amount of water is necessary. Namely, although the hydrolysis reaction proceeds even at a hydrolysis temperature lower than 40° C., this reaction proceeds at a reduced rate and necessitates much time and water before the reaction is completed. Such too low temperatures are hence impracticable. Meanwhile, the higher the hydrolysis temperature, the higher the rate of the hydrolysis reaction. Higher temperatures are hence preferred because the hydrolysis can be carried out in a short period. However, elevating the temperature beyond a certain level brings about no increase in reaction rate. Use of higher temperatures hence has a limited effect.

In the case where the reaction is conducted in a water solvent system using a temperature higher than 100° C., equipment for pressurization is required in order to maintain the liquid phase, resulting in the necessity of an enormous investment in the equipment. Furthermore, too high temperatures arouse fears about elimination of sulfo groups from the cation-exchange resin and deterioration of the resin itself.

The hydrolysis reaction may be conducted either batchwise or continuously. However, the batch reaction is preferred because the apparatus and operation are simple.

In the case of the continuous reaction, the hydrolysis is conducted, for example, by passing water through a fixed bed constituted of the modified sulfonic-acid-form cation-exchange resin. In general, however, a large amount of water is frequently required. Conditions for water passing in this case vary depending on reaction temperature. However, it is preferred to pass water at a liquid hourly space velocity (LHSV) of generally 0.01-10 $hr^{-1}$, especially 0.1-5 $hr^{-1}$.

In the case of the batch reaction, the hydrolysis can be conducted, for example, by stirring the modified sulfonic-acid-form cation-exchange resin in a water solvent. It is preferred that the reaction period should be 0.5-6 hours, especially 1-4 hours.

In either case, when the reaction period is too short, the hydrolysis does not proceed sufficiently and the desired acidic catalyst which has a high conversion in hydrolysis cannot be obtained. Even when the reaction period is excessively prolonged, the hydrolysis reaction does not proceed any more and the treatment period is uselessly long to render the treatment inefficient.

It is preferred in the invention that the sulfonic-acid-form cation-exchange resin and the modifier compound obtained by protecting the thiol group of at least any one of 2-pyridylalkanethiol compounds and 3-pyridylalkanethiol compounds with an acyl group should be stirred especially in a water solvent with heating to thereby simultaneously conduct modification and hydrolysis. In this case, it is preferred that water should be added in an amount of preferably 0.5-100 times by weight, more preferably 1-10 times by weight, the amount of the sulfonic-acid-form cation-exchange resin as stated above, and that the compound serving as a modifier be added to the water/resin mixture system and the resultant mixture be stirred at 40-100° C., preferably 50-95° C., more preferably 70-85° C., for 0.5-6 hours, in particular, 1-4 hours.

In the invention, the ratio of modification (degree of modification) of a sulfonic-acid-form cation-exchange resin with the compound obtained by protecting the thiol group of at least any one of 2-pyridylalkanethiol compounds and 3-pyridylalkanethiol compounds with an acyl group is not particularly limited as in the case of the above-described modification of a sulfonic-acid-form cation-exchange resin with at least any one of 2-pyridylalkanethiol compounds and 3-pyridylalkanethiol compounds. However, the ratio of modification thereof is such that preferably 3 mol % or more, more preferably 5 mol % or more, of all sulfo groups of the sulfonic-acid-form cation-exchange resin are modified. The ratio of modification thereof is preferably 70 mol % or less, more preferably 50 mol % or less, especially preferably 30 mol % or less.

The degree of modification can be controlled by regulating the amount of the compound to be used as a modifier for the sulfonic-acid-form cation-exchange resin in the modification reaction, the compound having been obtained by protecting the thiol group of at least any one of 2-pyridylalkanethiol compounds and 3-pyridylalkanethiol compounds with an acyl group, and by regulating reaction period, etc. in the modification reaction.

The conversion in hydrolysis of the sulfonic-acid-form cation-exchange resin modified with the compound obtained by protecting the thiol group of at least any one of 2-pyridylalkanethiol compounds and 3-pyridylalkanethiol compounds with an acyl group (proportion of the acyl groups converted to thiol groups by hydrolysis in the acyl groups introduced into the sulfonic-acid-form cation-exchange resin) is preferably 60% or higher, more preferably 80% or higher, especially preferably 90% or higher.

In the case where the conversion thereof is low, a carboxylic acid or a carboxylic acid derivative is liberated in the course of the reaction for bisphenol compound production and comes into the reaction system. The liberated acid or derivative is causative of quality decreases due to decomposition of the bisphenol compound, formation of isomers represented by a 2,4'-bisphenol compound, etc., and of corrosion of the production apparatus. Ideally, the conversion thereof is 100%. The conversion can be attained by regulating the modification period while using a modification temperature in the range of 40-100° C. according to the invention.

(4) Reaction between Phenol Compound and Carbonyl Compound

In the invention, the sulfonic-acid-form cation-exchange resin described above which has been modified with at least any one of 2-pyridylalkanethiol compounds and 3-pyridylalkanethiol compounds is packed into a reactor, and a phenol compound and a carbonyl compound are continuously fed thereto and reacted with each other to produce a bisphenol compound.

The invention has a remarkable effect that the catalyst suffers little decrease in catalytic activity when used over a prolonged period, and can be used while retaining a high conversion over the prolonged period. The term "prolonged period" herein means 2,000 hours or longer when the phenol compound has a high purity, or means 300 hours or longer when at least part of the phenol compound is phenol obtained when a bisphenol compound was purified.

The mode in which the phenol compound and the carbonyl compound are reacted in the invention is not particularly limited so long as the phenol compound and the carbonyl compound are continuously fed to a reactor packed with the sulfonic-acid-form strong cation-exchange resin as an acidic catalyst and are reacted therein. For example, use may be made of any of the fixed-bed flow-through mode, fluidized-bed mode, and continuous-stirring mode.

In the case where the reaction between a phenol compound and a carbonyl compound is conducted in the fixed-bed flow-through mode, fluidized-bed mode, and continuous-stirring mode, a mixture of the starting materials is fed at an LHSV of generally 0.05 $hr^{-1}$ or higher, preferably 0.2 $hr^{-1}$ or higher, based on the sulfonic-acid-form strong cation-exchange resin in the state of being wet with the phenol compound. The LHSV thereof is generally 20 $hr^{-1}$ or less, preferably 10 $hr^{-1}$ or less.

In the case where the reaction between a phenol compound and a carbonyl compound is conducted in the fixed-bed flow-through mode, a screen or the like may be disposed in at least either of upper and lower parts of the apparatus according to need so that only the liquid reaction mixture can pass through while preventing the packed sulfonic-acid-form strong cation-exchange resin from flowing out of the apparatus. The liquid reaction mixture may be caused to flow from the upper part to the lower part of the apparatus (down-flow system) or to flow from the lower part to the upper part of the apparatus (up-flow system).

The phenol compound and the carbonyl compound may be separately fed to the reactor, or may be fed as a mixture thereof.

In the invention, a phenol compound and a carbonyl compound are continuously fed to a reactor packed with the sulfonic-acid-form strong cation-exchange resin to produce a bisphenol compound. With respect to modes of reaction, it is known to conduct the reaction in the batch mode. However, by continuously reacting the starting materials, a bisphenol compound can be efficiently produced as compared with the case in which the reaction is conducted in the batch mode.

With respect to reaction temperature, the reaction is usually conducted at a temperature at which the reaction solution can be present in a liquid state without solidifying. In the case where the phenol compound is phenol, the reaction temperature is preferably 40° C. or higher, more preferably 60° C. or higher. Higher reaction temperatures are advantageous from the standpoint of reaction rate. However, from the standpoint of the heat resistance temperature of the ion-exchange resin, it is preferred to react the starting materials under such conditions that the maximum temperature within the reactor is preferably 120° C. or lower, more preferably 100° C. or lower. At higher reaction temperatures, the sulfonic-acid-from strong cation-exchange resin partly undergoes elimination of sulfo groups therefrom due to decomposition or the like even when the temperatures are not higher than the heat resistance temperature of the resin. Although the lowest possible temperature is preferred from this standpoint, there are the cases where the bisphenol compound which has been yielded solidifies when the temperature is too low.

The phenol compound to be used in the process for bisphenol compound production of the invention (a phenol compound which is not the phenol compound recovered and used within the bisphenol production process as will be described later) can be used as it is so long as the phenol compound has a high purity. However, it is generally preferred to purify the phenol compound before use. Methods for purifying the phenol compound are not particularly limited. Examples thereof include a method in which the phenol compound is reacted with an acidic catalyst such as a general sulfonic-acid-form cation-exchange resin at 40-110° C. to convert the impurities contained in the phenol compound into heavy matter and is then distilled to remove the heavy matter. The phenol compound thus obtained is fed to the reactor and thereby used as a starting material.

As the phenol compound to be used in the process for bisphenol compound production of the invention, a phenol compound recovered in a step for bisphenol compound production can be recycled and used. As the phenol compound to be recycled, use can be made of a phenol solution obtained by separating the target bisphenol compound from the liquid resulting from a reaction. (In the case where the bisphenol compound was separated by solidifying the bisphenol compound by crystallization or the like and subjecting the resultant mixture to solid-liquid separation in a solid-liquid separation step, the residual liquid is generally called "mother liquor". Other methods include a method in which the bisphenol compound is separated by distillation. Separation methods are not limited to these.) Incidentally, the phenol compound thus purified can be used in desired manners according to processes. For example, the purified phenol compound is used as a cleaning liquid for crystals obtained in the solid-liquid separation step and is recycled to the reactor together with the mother liquor.

In this case, it is preferred that the recovered phenol compound should be wholly or partly treated with an acid or alkali catalyst, subsequently subjected to removal of impurities, e.g., heavy matter, therefrom and further to recovery of a bisphenol compound, and then used as a starting material for a bisphenol compound. In the case where the phenol compound recovered within a process is recycled and used as a cleaning liquid for crystals obtained in a solid-liquid separation step, it is generally preferred to purify the phenol compound and then use the purified phenol compound.

When the process for bisphenol compound production is practiced on a small scale as in laboratories, a high-purity phenol compound which has been purified or the like is also used as a starting-material phenol compound. However, when the process is practiced on an industrial scale, it is usually advantageous to recycle and use a phenol compound recovered within the process.

It is known that use of a purified phenol compound results in little formation of impurities, is advantageous to the reaction, and is capable of preventing catalyst deactivation, as stated above, and this applies to the process of the invention. However, it has been found that even when compounds other than the required phenol compound are fed in a specific concentration to the reactor in the invention, a bisphenol compound can be continuously produced stably with a high conversion and high selectivity over a longer period than in the case where 4-pyridylethanethiol was used.

Especially when the phenol compound is phenol and at least one of bisphenol A (4,4'-bisphenol A), 2,4'-bisphenol A, and p-isopropylphenol is fed to the reactor together with phenol, then the process of the invention is capable of maintaining activity over a prolonged period as compared with processes in which use is made of catalysts obtained by modifying a sulfonic-acid-form cation-exchange resin with 2-aminoethanethiol and 4-pyridylethanethiol, which are conventionally known as modifiers. The process of the invention is preferred in this respect. Since the invention has such a feature, the process of the invention is especially preferred in the case where at least part of the phenol compound is a phenol compound obtained when a bisphenol compound was purified, that is, the case where a phenol compound recovered within the process is recycled and used, as described above.

In the invention, when the phenol compound is phenol and when at least one of bisphenol A (4,4'-bisphenol A), 2,4'-bisphenol A, and p-isopropylphenol is fed to the reactor together with phenol, then the amounts of these ingredients are as follows. The lower limit of the amount of the bisphenol A (4,4'-bisphenol A) per 100 parts by weight of the phenol is generally 0.3 parts by weight, preferably 1 part by weight, more preferably 3 parts by weight, even more preferably 5 parts by weight, especially preferably 7 parts by weight, and the upper limit thereof is generally 20 parts by weight, preferably 18 parts by weight, more preferably 15 parts by weight.

The lower limit of the amount of the 2,4'-bisphenol A per 100 parts by weight of the phenol is generally 0.3 parts by weight, preferably 0.5 parts by weight, more preferably 1 part by weight, even more preferably 1.5 parts by weight, especially preferably 2 parts by weight, and the upper limit thereof is generally 10 parts by weight, preferably 8 parts by weight, more preferably 5 parts by weight.

The lower limit of the amount of the p-isopropylphenol per 100 parts by weight of the phenol is generally 0.1 part by weight, preferably 0.2 parts by weight, and the upper limit thereof is generally 5 parts by weight, preferably 3 parts by weight, more preferably 2 parts by weight, even more preferably 1 part by weight, especially preferably 0.5 parts by weight.

Furthermore, the lower limit of the sum of the bisphenol A (4,4'-bisphenol A), 2,4'-bisphenol A, and p-isopropylphenol per 100 parts by weight of the phenol is generally 1 part by weight, preferably 3 parts by weight, more preferably 5 parts by weight, even more preferably 8 parts by weight, and the upper limit thereof is generally 35 parts by weight, preferably 30 parts by weight, more preferably 25 parts by weight, even more preferably 20 parts by weight.

Meanwhile, in the case where substances having an unknown structure coexist with those ingredients, the lower limit of the amount of the substances having an unknown structure, per 100 parts by weight of the phenol, is generally 0.3 parts by weight, preferably 1 part by weight, more preferably 1.5 parts by weight, even more preferably 2 parts by weight, especially preferably 3 parts by weight, and the upper limit thereof is generally 10 parts by weight, preferably 8 parts by weight, more preferably 6 parts by weight.

Furthermore, the lower limit of the sum of bisphenol A (4,4'-bisphenol A), 2,4'-bisphenol A, p-isopropylphenol, and substances having an unknown structure, per 100 parts by weight of the phenol, is generally 1 part by weight, preferably 3 parts by weight, more preferably 5 parts by weight, even more preferably 10 parts by weight, especially preferably 15 parts by weight, and the upper limit thereof is generally 45 parts by weight, preferably 35 parts by weight, more preferably 30 parts by weight, even more preferably 25 parts by weight.

In the case where those compounds are eliminated to concentrations lower than the lower limits in terms of relative amount based on the phenol, an additional purification step or the like is required. Such purification is hence undesirable. When those compounds are contained in concentrations higher than the upper limits in terms of relative amount based on the phenol, there are the cases where bisphenol A (4,4'-bisphenol A), 2,4'-bisphenol A, and an adduct of bisphenol A with phenol are precipitated as crystals within the reaction system, making it difficult to continue the operation. Such high concentrations of those compounds are hence undesirable. There are also the cases where purification is difficult when bisphenol A is produced as a product.

The liquid reaction mixture produced by the method described above contains the starting materials remaining unreacted, impurities formed during the reaction, etc. besides the phenol present in large excess. It is therefore necessary to take out the target bisphenol compound from the solution of these substances. Methods for separating the bisphenol compound as a target substance from the reaction mixture and purifying the compound are not particularly limited, and the separation and purification may be conducted in accordance with known methods. The case in which the target substance is bisphenol A is explained below as an example.

Subsequently to the reaction, the reaction mixture obtained through the reaction is separated into a fraction containing bisphenol A and phenol and a low-boiling fraction containing water formed as a by-product of the reaction, unreacted acetone, etc., in a low-boiling-fraction separation step. It is preferred that the low-boiling-fraction separation step should be conducted by a method in which a low-boiling fraction is separated by distillation under vacuum. The low-boiling fraction may contain phenol, etc. According to need, the bisphenol A concentration of the fraction containing bisphenol A and phenol can be regulated to a desired concentration by removing the phenol by further subjecting the fraction to distillation, etc., or by adding phenol thereto.

Subsequently, in a crystallization step, a slurry containing crystals of an adduct of bisphenol A with phenol is obtained. The bisphenol A concentration of the fraction which contains bisphenol A and phenol and is to be subjected to the crystallization step is preferably 10-30% from the standpoints of the handleability of the slurry to be obtained, etc. Examples of methods for crystallization include: a method in which the fraction containing bisphenol A and phenol is directly cooled; a method in which another solvent, e.g., water, is mixed therewith and this solvent is vaporized to thereby cool the fraction; a method in which the phenol is removed to concentrate the fraction; and a method in which these methods are conducted in combination. Crystallization may be conducted once or two or more times in order to obtain the adduct having a desired purity.

The slurry obtained in the crystallization step is subjected to a solid-liquid separation step, in which the slurry is separated into a solid and a liquid, i.e., crystals of the adduct and the mother liquor, by vacuum filtration, pressure filtration, centrifugal filtration, or the like, and the crystals of the adduct of bisphenol A with phenol are recovered. It is also possible to directly obtain crystals of bisphenol A by crystallization.

The adduct crystals obtained in the solid-liquid separation step are subjected to a phenol removal step, as the succeeding step, in which the crystals are melted and the phenol is thereafter removed by a technique such as flash distillation, thin-film distillation, steam stripping, etc. Thus, molten bisphenol A having a high purity is obtained. The phenol removed can be subjected to the reaction, cleaning of the adduct crystals obtained in the solid-liquid separation step, etc., after having been purified according to desire.

The high-purity molten bisphenol A obtained is solidified in a granulation step. A simple and preferred method is to eject the molten bisphenol A from a nozzle and contact the ejected melt with a cooling gas to thereby obtain bisphenol A prills in the form of small spheres. It is also possible to obtain bisphenol A from the adduct crystals obtained in the solid-liquid separation step, without via the phenol removal step, by subjecting the adduct crystals to crystallization again to crystallize the bisphenol A only.

For the purpose of preventing accumulation of impurities within the system, at least part of the mother liquor separated in the solid-liquid separation step may be treated in an impurity treatment step. For example, an alkali or an acid is mixed with the mother liquor, and the mixture is heat-treated and then distilled to separate the mixture into a light fraction and a heavy fraction. The light fraction is subjected to a recombination reaction treatment with an acid catalyst or the like and then used for reaction. This method is preferred also from the standpoint of profitability. In this method, by purging the heavy fraction from the system, accumulation of impurities can be prevented and the purity of the product can be improved. It is also possible to subject at least part of the mother liquor to isomerization with an acid catalyst and then to crystallization to thereby improve the recovery of the bisphenol A.

The low-boiling fraction obtained in the low-boiling-fraction separation step may be subjected to an acetone circulation step, in which the acetone remaining unreacted is separated and recovered and the recovered acetone can be circulated to a reaction step.

EXAMPLES

The invention will be explained below in detail by reference to Examples. However, the invention should not be construed as being limited by the following Examples in any way.

Example 1

Example 1-1

Preparation of 2-Pyridylethanethiol-Modified Cation-Exchange Resin

Into a 200-mL four-necked flask equipped with a nitrogen gas introduction tube were introduced 20.0 g, in terms of wet-state amount, of a gel-form strongly acidic cation-exchange resin having a degree of crosslinking of 4% manufactured by Mitsubishi Chemical Corp. (trade name, SK104; exchange capacity, 1.67 meq/g (wet state)) and about 60 mL of 60° C. desalted water. The strongly acidic cation-exchange resin was washed. The washings were discarded by decantation, and about 60 mL of 60° C. desalted water was introduced again. This washing operation was conducted three times. Subsequently, after the washings were discarded, 60 mL of desalted water was introduced and the atmosphere within the flask was replaced with nitrogen. Into this flask was introduced 0.73 g (5.24 mmol) of 2-pyridylethanethiol manufactured by Toronto Research Chemicals Inc., as a promoter, at a time while stifling the contents. The resultant mixture was further stirred for 2 hours at room temperature to conduct a modification treatment. After completion of the treatment, the modified cation-exchange resin obtained was washed with desalted water. Thus, a 2-pyridylethanethiol-modified cation-exchange resin catalyst (degree of modification, 15.7%) was obtained.

The degree of modification was determined from the amount of the gel-form strongly acidic cation-exchange resin subjected to the modification, the amount of the promoter added, and the amount of sulfo groups contained in the gel-form strongly acidic cation-exchange resin and determined by titration, in accordance with the following equation. The amount of sulfo groups contained in the gel-form strongly acidic cation-exchange resin corresponds to the exchange capacity.

Degree of modification (%)=[(amount of the promoter added (mmol))/{(amount of sulfo groups in the gel-form strongly acidic cation-exchange resin (meq/g (wet state))×(weight of the gel-form strongly acidic cation-exchange resin subjected to modification (g (wet state)))}]×100

<Production of Bisphenol Compound>

Figure 2:
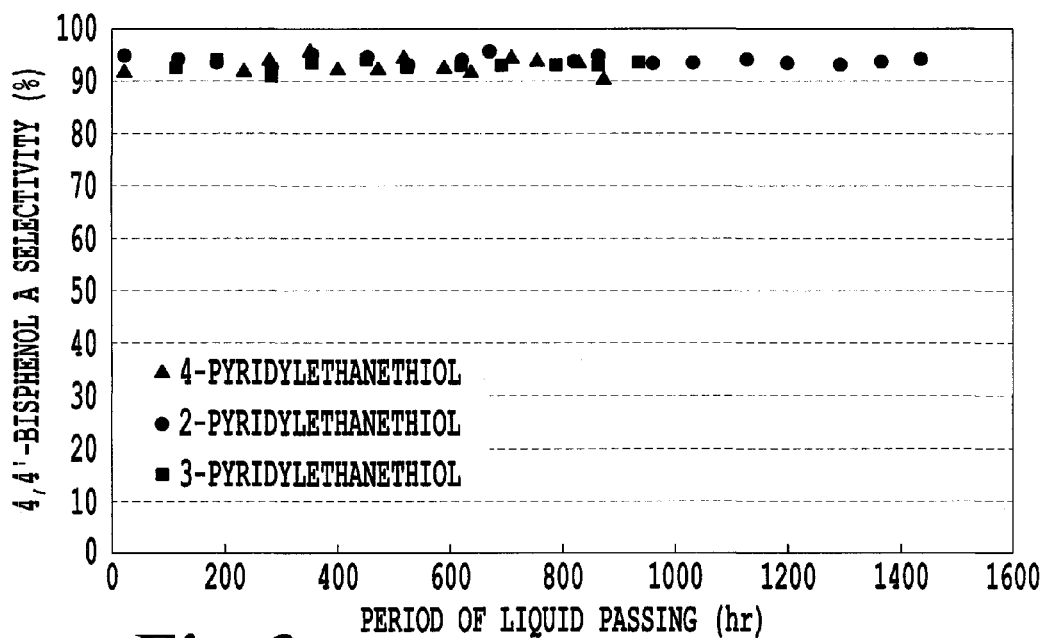
FIG. 2 is a presentation showing the changes with time of selectivity to bisphenol A which were observed in Examples 1-1 and 1-2 and Comparative Example 1-1

Into a stainless-steel column having an inner diameter of 1 cm and an overall length of 44 cm was packed 7.5 mL of the 2-pyridylethanethiol-modified cation-exchange resin prepared (hereinafter often referred to as "catalyst"). Phenol having a temperature of 60° C. was passed at 26 mL/hr through the catalyst-packed reactor from the upper part thereof for 24 hours to completely replace the moisture remaining in the catalyst with phenol. Thereafter, a liquid mixture having a phenol/acetone ratio (by mole) of 11 (4.3 wt % acetone, 79.4 wt % phenol, 10 wt % 4,4'-bisphenol A, and 6.3 wt % other substances (3.0 wt % 2,4'-bisphenol A, 0.25 wt % p-isopropylphenol, and substances of unknown structure as the remainder)) was continuously passed at 73° C. and 26 mL/hr from the upper part of the reactor by the down-flow method and reacted. A liquid reaction mixture was collected through the lower part of the reactor and analyzed by gas chromatography under the following conditions. The results thereof are shown in FIG. 1 and FIG. 2. Incidentally, the acetone conversion and the bisphenol A selectivity were determined using the following equations.

<Analysis Method>

Gas chromatograph: "GC-14B", manufactured by Shimadzu Corp.

Column: "Ultra Performance Capillary Column Ultra 2 (Cross-linked 5%-Phenylmethyl Silicone) 25 m×0.32 mm×0.52 μm", manufactured by Hewlett Packard Detector: FID Carrier gas: He Acetone conversion (%)=[{(number of moles of acetone in 1 kg of starting materials)−(number of moles of acetone in 1 kg of yielded liquid)}/ (number of moles of acetone in 1 kg of starting-material liquid)]×100

Bisphenol A selectivity (%)=[(number of moles of bisphenol A in 1 kg of yielded liquid)-(number of moles of bisphenol A in 1 kg of starting-material liquid)]/[(number of moles of acetone in 1 kg of starting-material liquid)-(number of moles of acetone in 1 kg of yielded liquid)]×100

Example 1-2

Synthesis of 3-Pyridylethanol

In order to synthesize 3-pyridylethanethiol, 3-pyridylethanol as an intermediate therefor was synthesized by the following method. Into a 1-L flask to which a nitrogen gas introduction tube, thermometer, Dimroth condenser, and dropping funnel had been attached was introduced 25.12 g (0.145 mol) of 3-pyridylacetic acid monohydrochloride. Thereto was added 500 mL of anhydrous methanol. After the atmosphere in the flask was replaced with nitrogen, the contents were stirred at room temperature to dissolve the monohydrochloride. Thereto was added dropwise 31.12 g (0.248 mol) of thionyl chloride. Thereafter, the resultant mixture was heated and reacted for further 2.5 hours with refluxing. After the reaction, the reaction mixture was cooled to room temperature, and the methanol was distilled off under vacuum. The residue was neutralized with a saturated aqueous solution of sodium hydrogen carbonate. An extraction operation using 100 mL of ethyl acetate was conducted three times, and anhydrous sodium sulfate was added to the resultant organic phase to dry the phase. The anhydrous sodium sulfate was removed by decantation. Thereafter, the solvent was distilled off under vacuum. Thus, 21.29 g (0.141 mol) of methyl 3-pyridylacetate, which is the methanol ester of 3-pyridylacetic acid, was obtained (yield, 97%).

Into a 500-mL flask to which a nitrogen gas introduction tube, thermometer, and Dimroth condenser had been attached were introduced 21.29 g (0.141 mol) of the methyl 3-pyridylacetate obtained above and 250 mL of anhydrous methanol. The contents were stirred at room temperature. The atmosphere in the flask was replaced with nitrogen, and 15.62 g (0.372 mol) of sodium borohydride was added to the contents little by little. The resultant mixture was heated and reacted for further 3.5 hours with refluxing. Thereafter, the liquid reaction mixture was cooled to room temperature, and 100 mL of water was added thereto to hydrolyze the excess sodium borohydride remaining unreacted. The methanol was distilled away under vacuum. Thereafter, an extraction operation using 100 mL of chloroform was conducted twice, and the resultant organic phase was washed with 100 mL of saturated aqueous sodium chloride solution and dried by adding anhydrous sodium sulfate thereto. The anhydrous sodium sulfate was removed by decantation. Thereafter, vacuum distillation was conducted to obtain 12.59 g (0.102 mol) of 3-pyridylethanol.

Synthesis of 3-Pyridylethanethiol

Using the 3-pyridylethanol obtained by the method described above, 3-pyridylethanethiol was produced by the following method.

Into a 500-mL flask to which a nitrogen gas introduction tube, thermometer, Dimroth condenser, and dropping funnel had been attached was introduced a liquid obtained by diluting 13.95 g (0.113 mol) of the 3-pyridylethanol obtained above with 100 mL of chloroform. The atmosphere in the flask was replaced with nitrogen. Thereafter, 19.10 g (0.153 mol) of thionyl chloride which had been diluted with 50 mL of chloroform was added dropwise to the contents with stirring at room temperature. After completion of the dropwise addition, the mixture was reacted for further 3 hours with stirring. Thereafter, 50 mL of ethanol was added to terminate the reaction. Fifty milliliters of toluene was added, and the mixture was subjected to vacuum distillation to remove substantially all of the ethanol and toluene. This operation was conducted again to obtain 20.12 g of crystals of 1-chloro-2-(3'-pyridyl)ethane hydrochloride.

Into a 500-mL flask to which a nitrogen gas introduction tube, thermometer, and Dimroth condenser had been attached were introduced 20.12 g of the crystals of 1-chloro-2-(3'-pyridyl)ethane hydrochloride obtained by the method described above, 200 mL of ethanol, 100 mL of water, and 25.41 g (0.223 mol) of potassium thioacetate. The atmosphere in the flask was replaced with nitrogen. Thereafter, the mixture was heated and refluxed for 4 hours. The ethanol was distilled away under vacuum, and the residual mixture was neutralized by adding 1N sodium hydroxide aqueous solution. An extraction operation using 100 mL of methylene chloride was conducted three times. Anhydrous sodium sulfate was added to the resultant organic phase to dry the phase, and the anhydrous sodium sulfate was removed by decantation. Thereafter, the solvent was distilled away under vacuum, and the residue was purified by column chromatography (packing material, silica gel; developer, hexane/ethyl acetate=1/1). Thus, 14.91 g (0.082 mol) of 3-pyridylethyl thioacetate, which is the ester of thioacetic acid with 3-pyridylethanol, was obtained in a yield of 73%.

The atmosphere in a 500-mL flask to which a nitrogen gas introduction tube, thermometer, Dimroth condenser, and dropping funnel had been attached was replaced with nitrogen. Thereafter, 3.12 g (82.3 mmol) of lithium aluminum hydride and 60 mL of anhydrous tetrahydrofuran were introduced thereinto, and the contents were stirred with cooling with ice. To the resultant solution was dropwise added, with cooling with ice, a solution prepared by dissolving 14.33 g (79.1 mmol) of the 3-pyridylethyl thioacetate obtained above in 50 mL of anhydrous tetrahydrofuran. After completion of the dropwise addition, the mixture was heated to 60° C. and stirred for 3 hours. After the reaction, the reaction mixture was cooled with ice, and 100 mL of water and 50 mL of acetic acid were added thereto. An extraction operation using 100 mL of ethyl acetate was conducted three times to thereby extract 3-pyridylethanethiol with the oil phase. This oil-phase liquid was neutralized with saturated aqueous sodium hydrogen carbonate solution, washed with 100 mL of saturated aqueous sodium chloride solution, and dried by adding anhydrous sodium sulfate thereto. The anhydrous sodium sulfate was removed by decantation. Thereafter, the ethyl acetate as the solvent was distilled off under vacuum, and the residue was purified by column chromatography (packing material, silica gel; developer, hexane/ethyl acetate=1/1). Thus, 8.92 g (64.1 mmol) of 3-pyridylethanethiol was obtained.

<Preparation of 3-Pyridylethanethiol-Modified Cation-Exchange Resin>

A 3-pyridylethanethiol-modified cation-exchange resin (degree of modification, 15.7%) was obtained in the same manner as in <Preparation of 2-Pyridylethanethiol-Modified Cation-Exchange Resin> of Example 1-1, except that the 3-pyridylethanethiol was used as a promoter in place of the 2-pyridylethanethiol.

<Production of Bisphenol Compound>

Reaction was conducted in the same manner as in <Production of Bisphenol Compound> of Example 1-1, except that the 3-pyridylethanethiol-modified cation-exchange resin (degree of modification, 15.7%) was used in place of the 2-pyridylethanethiol-modified cation-exchange resin (degree of modification, 15.7%). The acetone conversion and the bisphenol A selectivity were determined in the same manners as in Example 1-1. The results thereof are shown in FIG. 1 and FIG. 2.

Comparative Example 1-1

Synthesis of 4-Pyridylethanethiol

A nitrogen gas introduction tube, thermometer, Dimroth condenser, and dropping funnel were attached to a 300-mL four-necked flask. Thereto were fed 102.9 g (0.315 mol) of 30% by weight aqueous sulfuric acid solution and 11.42 g (0.15 mol) of thiourea. In a nitrogen atmosphere, the contents were heated to 70° C. with stirring, and 12.62 g (0.12 mol) of 4-vinylpyridine was then added dropwise thereto through the dropping funnel over about 1 hour while maintaining a reaction temperature of 70° C. Thereafter, the mixture was continuously reacted for 5 hours while maintaining 70° C. The resultant liquid reaction mixture was cooled to room temperature, and 30 mL of toluene was thereafter added thereto.

Furthermore, 45.74 g of 28% by weight ammonia water (0.75 mol in terms of ammonia) was added dropwise to the liquid reaction mixture over about 2 hours with stirring while taking care that the liquid temperature did not rise. After completion of the dropwise addition, the mixture was heated to 40° C. and stirred for 3 hours. After the stirring was stopped, the liquid reaction mixture was transferred to a separatory funnel and separated into two phases. The upper phase (toluene phase) was taken out, and the lower phase (water phase) was repeatedly extracted with 30 mL of toluene twice.

Subsequently, the toluene was distilled away with a rotary evaporator under the conditions of a bath temperature of 50° C. and a pressure of 12.5-1.1 kPa. The resultant residue was purified by distillation using a thin-film evaporator under the conditions of a wall surface temperature of 130° C. and a pressure of 0.6 kPa. As a result, 15.6 g of 4-pyridylethanethiol having a purity of 95.2% was obtained. The yield thereof based on the 4-vinylpyridine which had been fed was 88.9%.

<Preparation of 4-Pyridylethanethiol-Modified Cation-Exchange Resin>

A 4-pyridylethanethiol-modified cation-exchange resin (degree of modification, 15.7%) was prepared in the same manner as in <Preparation of 2-Pyridylethanethiol-Modified Cation-Exchange Resin> of Example 1-1, except that the 4-pyridylethanethiol obtained above was used as a promoter in place of the 2-pyridylethanethiol.

<Production of Bisphenol Compound>

Reaction and analysis were conducted in the same manners as in Example 1-1, except that the 4-pyridylethanethiol-modified cation-exchange resin obtained above was used in place of the 2-pyridylethanethiol-modified cation exchange resin. The results thereof are shown in FIG. 1 and FIG. 2.

As a result of use of the sulfonic-acid-form cation-exchange resins modified with 2-pyridylethanethiol, 3-pyridylethanethiol, or 4-pyridylethanethiol as acidic catalysts, it was found that the initial acetone conversion in the bisphenol A formation reaction was highest with the catalyst modified with 4-pyridylethanethiol, the second highest conversion was attained with the catalyst modified with 3-pyridylethanethiol, and the lowest conversion with the catalyst modified with 2-pyridylethanethiol. It was found from FIG. 2 that these catalysts were all equal in selectivity even when the reaction was conducted continuously over a prolonged period. However, in the case where the reaction was conducted continuously over a prolonged period, use of the 2-pyridylethanethiol-modified cation-exchange resin and the 3-pyridylethanethiol-modified cation-exchange resin as acidic catalysts resulted in a smaller decrease in acetone conversion than use of the 4-pyridylethanethiol-modified cation-exchange resin as an acidic catalyst. Namely, the former catalysts were inhibited from deteriorating and were hence found to be usable over a prolonged period while maintaining a high conversion.

Example 1-3

Evaluation of Heat Resistance of Pyridylethanethiols

Figure 3:
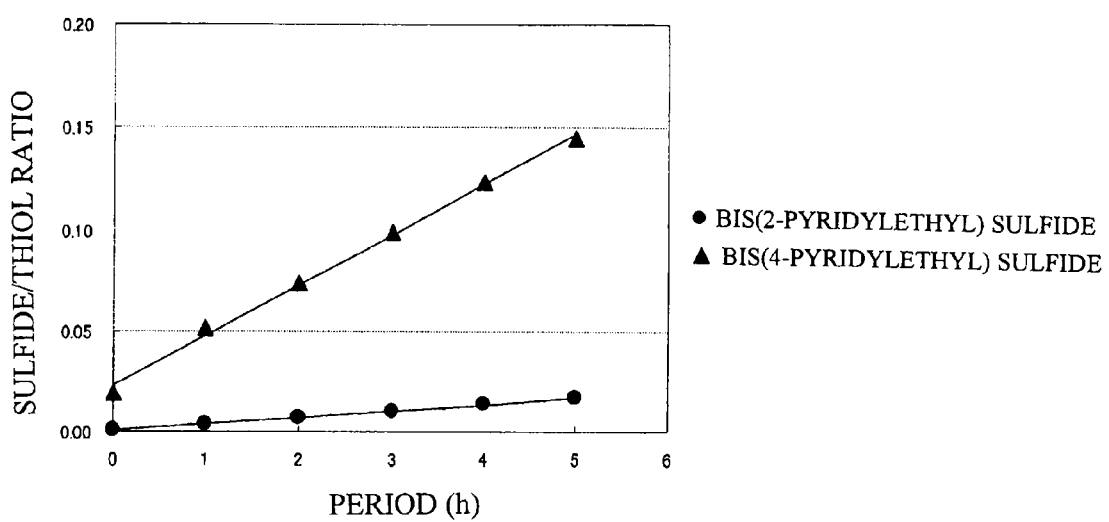
FIG. 3 is a presentation showing the result of the evaluation of heat resistance of pyridylethanethiols conducted in Example 1-3.

Into a 100-mL three-necked flask the atmosphere in which had been replaced with nitrogen was introduced 60 g of 2-pyridylethanethiol prepared in the same manner as in Example 3-1, which will be given later. In a nitrogen atmosphere, the contents were heated to 100° C. with an oil bath while stirring the contents with a magnetic stirrer. After initiation of the heating, sampling was conducted at an interval of 1 hour. Each sample was analyzed to determine the concentration therein of a sulfide derived from the 2-pyridylethanethiol, by gas chromatography under the following conditions. The same evaluation was conducted with respect to 4-pyridylethanethiol. The results thereof are shown in FIG. 3.

<Analysis Method>

Gas chromatograph: "GC-14A", manufactured by Shimadzu Corp.

Column: "TC-5 (5% Diphenyl-95% Dimethylpolysiloxane) 60 m×0.32 mm×1.00 μm", manufactured by GL Sciences Detector: FID Carrier gas: He Sulfide/thiol ratio=(area of sulfide GC peak)/(area of thiol GC peak)

As shown in FIG. 3, it was found that the amount of the sulfide formed in the 2-pyridylethanethiol in 5 hours during the heating was about ⅛ the sulfide formed in the 4-pyridylethanethiol. The results indicate that 2-pyridylethanethiol is less apt to suffer thermal alteration from thiol to sulfide and has excellent heat resistance, as compared with 4-pyridylethanethiol, which is an isomer.

In the case where a pyridylethanethiol is fixed to a strongly acidic ion-exchange resin and this resin is used as a catalyst for a bisphenol, this catalyst has the effect of accelerating the reaction for bisphenol production, only when the pyridylethanethiol is in the thiol state. After the pyridylethanethiol has altered to a sulfide, this catalyst does not have the effect of accelerating the reaction for bisphenol production. Since the reaction for bisphenol production is an exothermic reaction, the catalyst is continuously exposed to heat and, hence, the pyridylethanethiol is gradually altered to a sulfide to deteriorate the catalyst performance. However, 2-pyridylethanethiol is less apt to suffer the thermal alteration from thiol to sulfide, and the catalyst hence is expected to be used over a prolonged period while retaining the highly active state.

<Test of Pyridylethanethiols Concerning Impurity>

(1) Evaluation Using Pure Phenol

Example 1-4

Figure 4A:
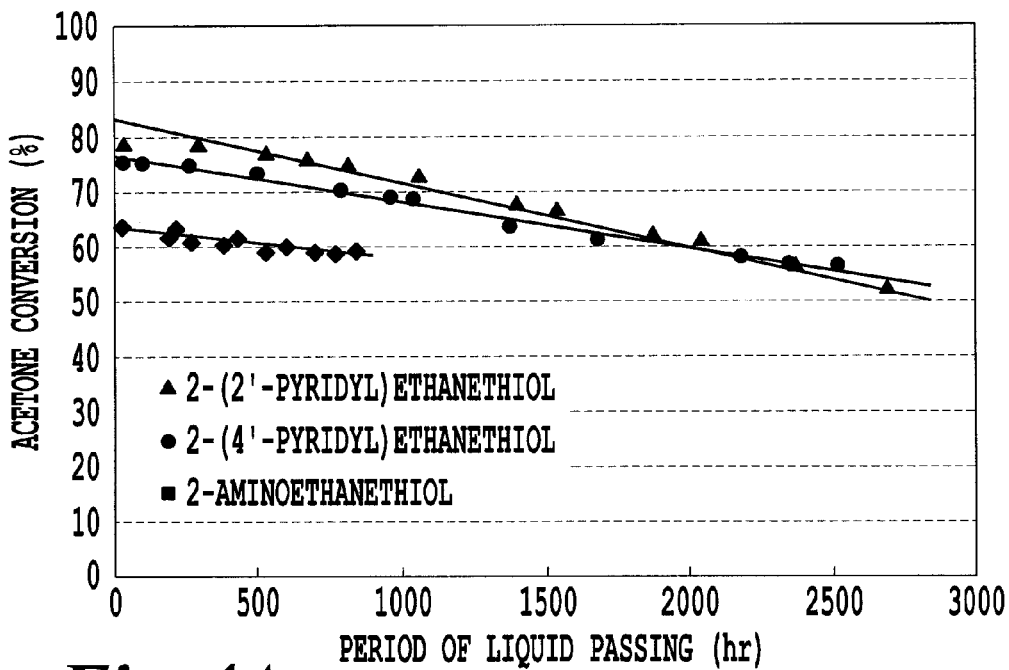
FIG. 4A is a presentation showing the changes with time of the conversion of acetone which were observed in Example 1-4 and Comparative Examples 1-2 and 1-3.
Figure 4B:
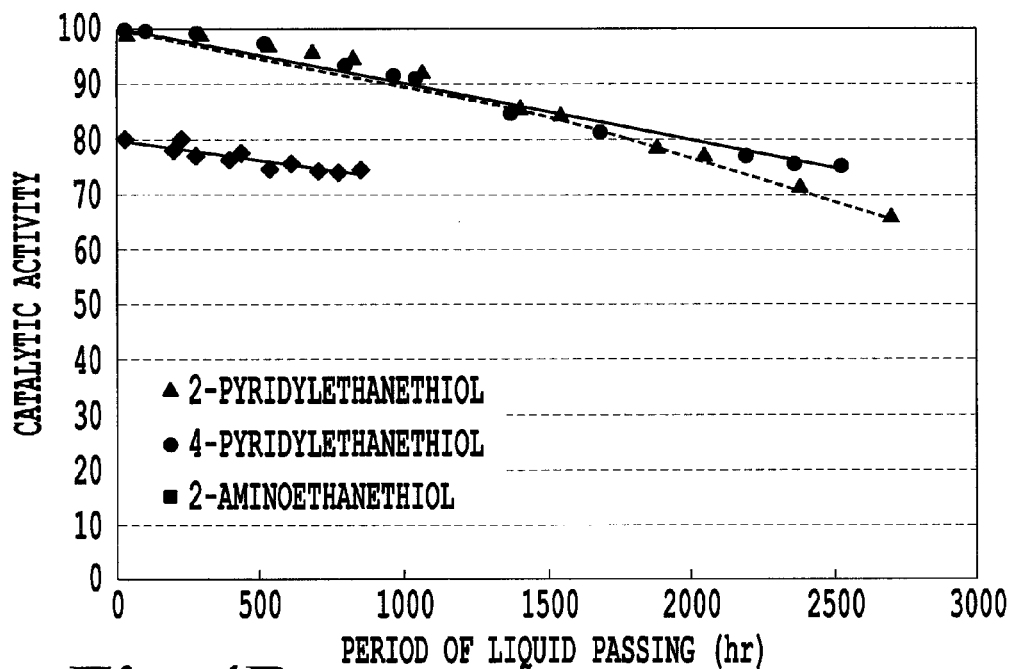
FIG. 4B is a presentation showing the changes with time of the catalytic activity on the conversion of acetone which were observed in Example 1-4 and Comparative Examples 1-2 and 1-3.

Into a stainless-steel column having an inner diameter of 1 cm and an overall length of 44 cm was packed 7.5 mL of a 2-pyridylethanethiol-modified sulfonic-acid-form cation-exchange resin prepared so as to have a degree of modification of 15%. Phenol having a temperature of 60° C. was passed at 26 mL/hr through the catalyst-packed reactor from the upper part thereof for 24 hours to completely replace the moisture remaining in the catalyst with phenol. Thereafter, a liquid mixture having a phenol/acetone ratio (by mole) of 13 (4.5 wt % acetone, 95.4 wt % phenol, up to 20 weight ppm 4,4'-bisphenol A, and 0.2 wt % other substances (up to 10 weight ppm 2,4'-bisphenol A, 0.02 wt % p-isopropylphenol, and substances of unknown structure as the remainder)) was continuously passed at 73° C. and 26 mL/hr from the upper part of the reactor by the down-flow method and reacted. In the course of the reaction, the liquid reaction mixture was suitably sampled, and each sample was examined for conversion to evaluate a change in catalytic activity. In FIG. 4A is shown the change in acetone conversion. In FIG. 4B is shown the transition in acetone conversion determined by taking the initial acetone conversion as 100.

Comparative Example 1-2

A change in catalytic activity was evaluated in the same manner as in Example 1-4, except that a 4-pyridylethanethiol-modified sulfonic-acid-form cation-exchange resin was used in place of the 2-pyridylethanethiol-modified sulfonic-acid-form cation-exchange resin. The change in acetone conversion is shown in FIG. 4A, and the transition of acetone conversion calculated in the same manner as in Example 1-4 is shown in FIG. 4B.

Comparative Example 1-3

A change in catalytic activity was evaluated in the same manner as in Example 1-4, except that a 2-aminoethanethiol-modified sulfonic-acid-form cation-exchange resin was used in place of the 2-pyridylethanethiol-modified sulfonic-acid-form cation-exchange resin. The change in acetone conversion is shown in FIG. 4A, and the transition of acetone conversion is shown in FIG. 4B. Incidentally, since the initial acetone conversion for the 2-aminoethanethiol-modified sulfonic-acid-form cation-exchange resin was lower by about 20% than the initial acetone conversion for the 2-pyridylethanethiol-modified sulfonic-acid-form cation-exchange resin, the evaluation of catalytic activity in FIG. 4B is shown so as to start at about 80.

As shown in FIG. 4A, it was found that the catalyst obtained by modifying a sulfonic-acid-form cation-exchange resin with 2-pyridylethanethiol was higher in acetone conversion than the catalyst obtained using 2-aminoethanethiol, which has conventionally been known as a modifier. Although the former catalyst was slightly inferior in initial activity to the catalyst obtained using 4-pyridylethanethiol, that catalyst suffers little decrease in activity when used over a prolonged period. The catalyst obtained using 2-pyridylethanethiol was found to be highly suitable for industrial use.

As shown in FIG. 4B, the catalyst obtained by modifying a sulfonic-acid-form cation-exchange resin with 2-pyridylethanethiol was found to be a catalyst which can retain activity over a prolonged period as compared with the catalysts obtained using 2-aminoethanethiol and 4-pyridylethanethiol, which have conventionally been known as modifiers.

(2) Evaluation Using Liquid Reaction Mixture Containing Impurities

Comparative Example 1-4

Figure 5:
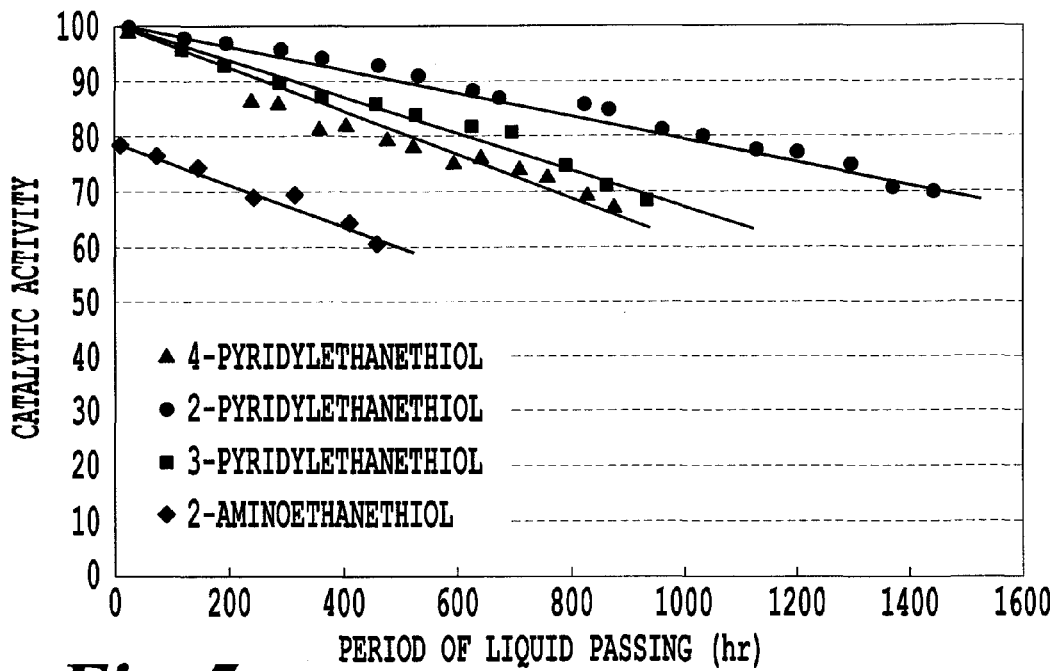
FIG. 5 is a presentation showing the changes with time of the catalytic activity on the conversion of acetone which were observed in Examples 1-1 and 1-2, Comparative Example 1-1, and Comparative Example 1-4.

A change in catalytic activity was evaluated in the same manner as in Example 1-1, except that a 2-aminoethanethiol-modified sulfonic-acid-form cation-exchange resin was used in place of the 2-pyridylethanethiol-modified sulfonic-acid-form cation-exchange resin. The transition of acetone conversion evaluated in the same manner as in FIG. 4B is shown in FIG. 5. Incidentally, since the initial acetone conversion for the 2-aminoethanethiol-modified sulfonic-acid-form cation-exchange resin was lower by about 20% than the initial acetone conversion for the 2-pyridylethanethiol-modified sulfonic-acid-form cation-exchange resin, the evaluation of catalytic activity is shown so as to start at about 80, as in FIG. 4B.

The evaluation of 2-pyridylethanethiol shown in FIG. 5 was obtained through calculations from values obtained in Example 1-1, and the evaluation of 3-pyridylethanethiol was obtained through calculations from values obtained in Example 1-2. Furthermore, the evaluation of 4-pyridylethanethiol was obtained through calculations from values obtained in Comparative Example 1-1. As shown in FIG. 5, the catalyst obtained by modifying a cation-exchange resin with 2-pyridylethanethiol was found to be a catalyst which, even when phenol containing impurities in some degree is used, can retain activity over a prolonged period as compared with the catalysts obtained by modifying a sulfonic-acid-form cation-exchange resin with 2-aminoethanethiol and 4-pyridylethanethiol, which have conventionally been known as modifiers, as in the case where pure phenol containing substantially no impurities is used as described under (1) above. Furthermore, the effect of retaining activity over a prolonged period on the impurity-containing phenol as compared with activity on pure phenol containing substantially no impurities was more remarkably produced by that catalyst than by the catalysts obtained by modifying a cation-exchange resin with 2-aminoethanethiol, 4-pyridylethanethiol, or the like.

The phenol used is phenol which contains impurities in substantially the same degree as the liquid (mother liquor) obtained by separating bisphenol A or crystals of a bisphenol A/phenol adduct, by solid-liquid separation, from the slurry discharged from the crystallization step. Consequently, it has become apparent that in the case where the mother liquor from a crystallization step is recycled to a reaction step and used again as a starting material, production of a bisphenol with the catalyst obtained by modifying a cation-exchange resin with 2-pyridylethanethiol is especially advantageous.

Example 2

In the following Examples 2-1 to 2-3 and Reference Example 2-1, the amount of polymers contained in the 2-vinylpyridine used as a starting material for 2-pyridylethanethiol was determined by the following GPC method and/or reprecipitation method.

<GPC Method>

An examination was made by gel permeation chromatography (GPC) under the following conditions. A calibration curve for use in polymer amount determination was drawn using a standard poly(2-vinylpyridine) sample (manufactured by Polymer Source Inc.; Mn=10,000, Mw=10,800, Mw/Mn=1.08). The amount of polymers having a molecular weight, calculated for standard polystyrene, of 2,000 or higher was determined by the absolute calibration curve method.

Apparatus: "LC-10AS", manufactured by Shimadzu Corp.
UV detector: "SPD-10A", manufactured by Shimadzu Corp.
Column: "TSKgelG2000HXL" (7.8 mm (diameter)×300 mm), manufactured by Tosoh Corp.
Mobile phase: tetrahydrofuran (for HPLC)
Flow rate: 0.8 mL/min
Column temperature: 40° C.
Detection wavelength: 254 nm
Sample: diluted 100 times by volume <Reprecipitation Method>

To 2-vinylpyridine (W1 g) was added a 10-fold amount by weight of n-hexane (purity, 99.5% or higher). The mixture was stirred. The resultant sediment was taken out by filtration through a membrane filter having a pore diameter of 0.1 µm ("H010A047A", manufactured by Toyo Roshi Kaisha, Ltd.). The sediment obtained was dried in a 60° C. thermostatic vacuum dryer for 3 hours to recover polymers (W2 g) contained in the 2-vinylpyridine. The content of the polymers was calculated using the following equation.

Content of polymers (wt %)=100×($W2$ (g))/($W1$ (g))

The purity of a crude 2-pyridylethanethiol product produced from 2-vinylpyridine was determined by gas chromatography (GC) analysis under the following conditions.

<GC Analysis>

Gas chromatograph: "GC-2014", manufactured by Shimadzu Corp.
Column: "TC-5" (60 m×0.32 mm×100 µm), manufactured by GL Sciences
Detector: FID
Carrier gas: He Example 2-1

2-Vinylpyridine having a polymer content determined by the GPC method of 0.24% by weight was used to produce 2-pyridylethanethiol. A stirring motor, a Dimroth condenser equipped with a nitrogen gas introduction tube, and a thermometer were attached to a jacketed four-necked separable flask (capacity, about 700 mL). Thereinto were introduced 254.2 g (0.75 mol) of 29% by weight aqueous sulfuric acid solution and 27.2 g (0.36 mol) of thiourea. In a nitrogen atmosphere, hot water was passed through the jacket to heat the contents to 70° C. with stirring, and 30.0 g (0.29 mol) of the 2-vinylpyridine was added dropwise thereto over about 2 hours using a syringe pump. Thereafter, the mixture was continuously reacted for 5 hours while keeping the temperature thereof at 70° C.

This liquid reaction mixture was cooled to room temperature. Thereafter, 51.7 g of toluene was added thereto, and this liquid reaction mixture was cooled further to 20° C. While stirring the liquid reaction mixture, 108.4 g of 28% by weight ammonia water (1.78 mol in terms of ammonia) was added dropwise thereto over about 2 hours while taking care that the liquid temperature did not rise. After completion of the dropwise addition, the mixture was heated to 40° C. and stirred for 3 hours. After the stirring was stopped, the liquid reaction mixture was transferred to a separatory funnel and separated into two phases. The upper phase (toluene phase) was taken out, and the lower phase (water phase) was extracted twice with 51.7 g of toluene.

The solid matter adherent to the inner wall of the flask and to the stirring blades was scratched off and recovered. As a result, the amount of the recovered solid matter was 0.62 g. The proportion thereof to the 2-vinylpyridine which had been fed was 2.1% by weight.

The whole toluene phase was collected, and the toluene was distilled away using a rotary evaporator at a bath temperature of 30-60° C. and a pressure of 1.0 kPa. As a result, 36.6 g of a crude 2-pyridylethanethiol product (purity, 94.2%) was obtained. The yield of the 2-pyridylethanethiol based on the 2-vinylpyridine fed was 86.8%.

Reference Example 2-1

2-Pyridylethanethiol was synthesized in the same manner as in Example 2-1, except that 2-vinylpyridine having a polymer content determined by the GPC method of 2.76% by weight and a polymer content determined by the reprecipitation method of 2.58% by weight was used as a starting material.

The solid matter adherent to the inner wall of the flask and to the stirring blades was recovered in an amount of 2.46 g, and the proportion thereof to the 2-vinylpyridine which had been fed was 8.2% by weight. The amount of the crude 2-pyridylethanethiol product obtained was 33.8 g (purity, 93.8%), and the yield thereof based on the 2-vinylpyridine fed was 79.8%.

Example 2-2

The 2-vinylpyridine used in Reference Example 2-1 was purified by simple distillation (temperature, 43° C.; pressure, 1.5 kPa). The purified 2-vinylpyridine was examined for polymers by the GPC method. As a result, no polymer was detected. 2-Pyridylethanethiol was synthesized in the same manner as in Example 2-1, except that the 2-vinylpyridine was used as a starting material.

The solid matter adherent to the inner wall of the flask and to the stirring blades was recovered in an amount of 0.20 g, and the proportion thereof to the 2-vinylpyridine which had been fed was 0.7% by weight. The amount of the crude 2-pyridylethanethiol product obtained was 35.5 g (purity, 95.0%), and the yield thereof based on the 2-vinylpyridine fed was 84.9%.

Example 2-3

2-Pyridylethanethiol was synthesized in the same manner as in Example 2-1, except that 2-vinylpyridine in which no polymer was detected by the GPC method and the reprecipitation method was used as a starting material.

The solid matter adherent to the inner wall of the flask and to the stirring blades was recovered in an amount of 0.03 g, and the proportion thereof to the 2-vinylpyridine which had been fed was 0.1% by weight. The amount of the crude 2-pyridylethanethiol product obtained was 35.3 g (purity, 96.5%), and the yield thereof based on the 2-vinylpyridine fed was 85.8%.

The results obtained in Examples 2-1 to 2-3 and Reference Example 2-1 are summarized in Table 1.

It was found from Table 1 that when 2-vinylpyridine having a polymer content of 2% by weight or less is used as a starting material in 2-pyridylethanethiol production, high-purity 2-pyridylethanethiol can be produced in high yield while inhibiting scale deposition within the production equipment.

TABLE 1

| | Polymer content of 2-vinylpyridine as starting material (wt %)* | | Solid content | | 2-Pyridyl-ethane-thiol yielded | |
|---|---|---|---|---|---|---|
| | GPC method | Reprecipitation method | Amount recovered (g) | Proportion to 2-vinylpyridine (wt %) | Purity (%) | Yield (%) |
| Example 2-1 | 0.24 | — | 0.62 | 2.1 | 94.2 | 86.8 |
| Example 2-2 | not detectable | — | 0.20 | 0.7 | 95.0 | 84.9 |
| Example 2-3 | not detectable | not detectable | 0.03 | 0.1 | 96.5 | 85.8 |
| Reference Example 2-1 | 2.76 | 2.58 | 2.46 | 8.2 | 93.8 | 79.8 |

*—: not determined

Example 3

In Examples 3-1 and 3-2 and Reference Example 3-1, the purity of a crude 2-pyridylethanethiol product produced from 2-vinylpyridine was determined by gas chromatography (GC) analysis under the same conditions as in Example 2.

Example 3-1

A stirring motor, a Dimroth condenser equipped with a nitrogen gas introduction tube, and a thermometer were attached to a jacketed four-necked separable flask (capacity, about 700 mL). Thereinto were introduced 254.2 g (0.75 mol) of 29% by weight aqueous sulfuric acid solution, 27.2 g (0.36 mol) of thiourea, and 51.7 g of toluene. In a nitrogen atmosphere, hot water was passed through the jacket to heat the contents to 70° C. with stirring, and 30.0 g (0.29 mol) of 2-vinylpyridine was added dropwise thereto over about 2 hours using a syringe pump. Thereafter, the mixture was continuously reacted for 5 hours while keeping the temperature thereof at 70° C.

The volume ratios of the water and the toluene to the 2-vinylpyridine in the liquid reaction mixture are as shown in Table 2.

This liquid reaction mixture was cooled to 20° C. While stirring the liquid reaction mixture, 108.4 g of 28% by weight ammonia water (1.78 mol in terms of ammonia) was added dropwise thereto over about 2 hours while taking care that the liquid temperature did not rise. After completion of the dropwise addition, the mixture was heated to 40° C. and stirred for 3 hours. After the stirring was stopped, the liquid reaction mixture was transferred to a separatory funnel and separated into two phases. The upper phase (toluene phase) was taken out, and the lower phase (water phase) was extracted twice with 51.7 g of toluene.

No adhesion of solid matter to the inner wall of the flask and to the stirring blades was observed in this reaction.

The whole toluene phase was collected, and the toluene was distilled away using a rotary evaporator at a bath temperature of 30-60° C. and a pressure of 1.0 kPa. As a result, 36.5 g of a crude 2-pyridylethanethiol product (purity, 95.8%) was obtained. The yield of the 2-pyridylethanethiol based on the 2-vinylpyridine fed was 87.8%.

Example 3-2

A stirring motor, a Dimroth condenser equipped with a nitrogen gas introduction tube, and a thermometer were attached to a jacketed four-necked separable flask (capacity, about 700 mL). Thereinto were introduced 254.2 g (0.75 mol) of 29% by weight aqueous sulfuric acid solution and 27.2 g (0.36 mol) of thiourea. In a nitrogen atmosphere, hot water was passed through the jacket to heat the contents to 70° C. with stirring, and a solution prepared by diluting 30.0 g (0.29 mol) of 2-vinylpyridine with 51.7 g of toluene was added dropwise thereto over about 1.2 hours using a syringe pump. Thereafter, the mixture was continuously reacted for 5 hours while keeping the temperature thereof at 70° C.

The volume ratios of the water and the toluene to the 2-vinylpyridine in the liquid reaction mixture are as shown in Table 2.

This liquid reaction mixture was cooled to 20° C. While stirring the liquid reaction mixture, 108.4 g of 28% by weight ammonia water (1.78 mol in terms of ammonia) was added dropwise thereto over about 2 hours while taking care that the liquid temperature did not rise. After completion of the dropwise addition, the mixture was heated to 40° C. and stirred for 3 hours. After the stirring was stopped, the liquid reaction mixture was transferred to a separatory funnel and separated into two phases. The upper phase (toluene phase) was taken out, and the lower phase (water phase) was extracted twice with 51.7 g of toluene.

After the reaction, the solid matter adherent to the inner wall of the flask and to the stirring blades was recovered by scratching. As a result, the amount of the recovered solid matter was 0.25 g. The proportion thereof to the 2-vinylpyridine which had been fed was 0.8% by weight.

The whole toluene phase was collected, and the toluene was distilled away using a rotary evaporator at a bath temperature of 30-60° C. and a pressure of 1.0 kPa. As a result, 36.5 g of a crude 2-pyridylethanethiol product (purity, 95.9%) was obtained. The yield of the 2-pyridylethanethiol based on the 2-vinylpyridine fed was 88.1%.

Reference Example 3-1

A stirring motor, a Dimroth condenser equipped with a nitrogen gas introduction tube, and a thermometer were attached to a jacketed four-necked separable flask (capacity, about 700 mL). Thereinto were introduced 254.2 g (0.75 mol) of 29% by weight aqueous sulfuric acid solution and 27.2 g (0.36 mol) of thiourea. In a nitrogen atmosphere, hot water was passed through the jacket to heat the contents to 70° C. with stirring, and 30.0 g (0.29 mol) of 2-vinylpyridine was added dropwise thereto over about 2 hours using a syringe pump. Thereafter, the mixture was continuously reacted for 5 hours while keeping the temperature thereof at 70° C.

This liquid reaction mixture was cooled to room temperature. Thereafter, 51.7 g of toluene was added thereto, and this liquid reaction mixture was cooled further to 20° C. While stirring the liquid reaction mixture, 108.4 g of 28% by weight ammonia water (1.78 mol in terms of ammonia) was added dropwise thereto over about 2 hours while taking care that the liquid temperature did not rise. After completion of the dropwise addition, the mixture was heated to 40° C. and stirred for 3 hours. After the stirring was stopped, the liquid reaction mixture was transferred to a separatory funnel and separated into two phases. The upper phase (toluene phase) was taken out, and the lower phase (water phase) was extracted twice with 51.7 g of toluene.

After the reaction, the solid matter adherent to the inner wall of the flask and to the stirring blades was recovered by scratching. As a result, the amount of the recovered solid matter was 0.96 g. The proportion thereof to the 2-vinylpyridine which had been fed was 3.2% by weight.

The whole toluene phase was collected, and the toluene was distilled away using a rotary evaporator at a bath temperature of 30-60° C. and a pressure of 1.0 kPa. As a result, 36.1 g of a crude 2-pyridylethanethiol product (purity, 93.1%) was obtained. The yield of the 2-pyridylethanethiol based on the 2-vinylpyridine fed was 85.5%.

The results obtained in Examples 3-1 and 3-2 and Reference Example 3-1 are summarized in Table 2.

It can be seen from Table 2 that by reacting 2-vinylpyridine with thiourea in the presence of water and a hydrocarbon solvent to obtain an isothiuronium salt and decomposing the resultant isothiuronium salt to obtain 2-pyridylethanethiol, it is possible to obtain high-purity 2-pyridylethanethiol in high yield while inhibiting scale deposition within the production equipment.

TABLE 2

| | Amount of solvent used relative to 2-vinylpyridine in reaction (volume ratio) | | Solid content | | 2-Pyridylethane-thiol yielded | |
|---|---|---|---|---|---|---|
| | | | Amount recovered | Proportion to 2-vinyl-pyridine | Purity | Yield |
| | Water | Toluene | (g) | (wt %) | (%) | (%) |
| Example 3-1 | 1 | 0.29 | 0 | 0 | 95.8 | 87.8 |
| Example 3-2 | 1 | 0.29 | 0.25 | 0.8 | 95.9 | 88.1 |
| Reference Example 3-1 | 1 | 0* | 0.96 | 3.2 | 93.1 | 85.5 |

*Toluene was added after reaction in amount of 0.29 in terms of volume ratio.

Example 4

Example 4-1-1

Synthesis of 2-Pyridylethyl Thioacetate

Into a 100-mL four-necked flask equipped with a nitrogen gas introduction tube, thermometer, Dimroth condenser, and dropping funnel was introduced 15.22 g (0.20 mol) of thioacetic acid (manufactured by Tokyo Kasei Kogyo Co., Ltd.). The contents began to be stirred, and nitrogen was introduced. Thereafter, the contents were cooled to 5° C. or lower with an ice bath, and 21.03 g (0.20 mol) of 2-vinylpyridine was added dropwise thereto through the dropping funnel over 1 hour. After completion of the dropwise addition, the ice bath was removed, and the mixture was stirred at room temperature for further 1 hour and reacted. After completion of the reaction, the liquid reaction mixture was subjected to vacuum distillation under the conditions of a bath temperature of 120° C. and a pressure of 0.8 kPa to obtain 27.8 g of 2-pyridylethyl thioacetate. As a result of analysis by gas chromatography, the 2-pyridylethyl thioacetate was found to have a purity of 96.8% and the yield thereof was found to be 78.2%.

Conditions of the gas chromatography and the method used for calculating the yield are shown below.
(Gas Chromatography)
  Apparatus: "GC-14A", manufactured by Shimadzu Corp.
  Column: "TC-5" (60 m×0.32 mm×1.0 μm), manufactured by GL Sciences
  Detector: FID
  Carrier gas: helium
(Calculation Method)

Yield (%)=[(number of moles of the 2-pyridylethyl thioacetate)/(number of moles of the thioacetic acid)]×100

<Preparation of Acidic Catalyst>

Into a 100-mL four-necked flask equipped with a nitrogen gas introduction tube were introduced 3.00 g, in terms of wet-state amount, of a sulfonic-acid-form cation-exchange resin (DIAION (registered trademark) "SK104H", manufactured by Mitsubishi Chemical Corp.; exchange capacity, 1.65 mmol/g (wet state)) and about 20 mL of 60° C. desalted water. The sulfonic-acid-form cation-exchange resin was washed, and the washings were discarded by decantation. This washing operation using about 20 mL of 60° C. desalted water was conducted three times. After the washings were discarded, about 20 mL of desalted water was introduced, and the atmosphere within the flask was replaced with nitrogen. Stirring was initiated. The contents were heated with a water bath so that the internal temperature of the flask was kept at 70° C. Using a syringe, 0.14 g (0.73 mmol) of the 2-pyridylethyl thioacetate prepared under the conditions shown above was added dropwise to the contents. After completion of the dropwise addition, the mixture was stirred for further 3 hours to conduct modification and a hydrolysis treatment. After completion of the modification and hydrolysis treatment, the sulfonic-acid-form cation-exchange resin was taken out by filtration to obtain an acidic catalyst, and the filtrate was recovered.

Methyl red-methylene blue was added as an indicator to the recovered filtrate, and titration analysis was conducted with 0.1N sodium hydroxide aqueous solution (titer: f). The amount of the acid in the filtrate and the conversion of the 2-pyridylethyl thioacetate in the hydrolysis were calculated from the dropped amount of the solution (A mL) required for the titration, using the following equations. As a result, the acid amount was found to be 0.66 mmol and the conversion in hydrolysis of the 2-pyridylethyl thioacetate was found to be 90.4%.

$$\text{Acid amount (mmol)}=(A \text{ (mL)})\times f\times 0.1$$

$$\text{Conversion (\%)}=[(\text{amount of acid in the filtrate (mmol)})/(\text{amount of the 2-pyridylethyl thioacetate added (mmol)})]\times 100$$

Incidentally, the degree of modification, which was calculated from the amount of the sulfonic-acid-form cation-exchange resin subjected to the modification, the amount of the modifier (2-pyridylethyl thioacetate) added, and the amount of the sulfo groups contained in the sulfonic-acid-form cation-exchange resin (exchange capacity) using the following equation, was 14.7%.

$$\text{Degree of modification (\%)}=[(\text{amount of the modifier added (mmol)})/\{(\text{amount of sulfo groups in the sulfonic-acid-form cation-exchange resin (mmol/g (wet state))})\times(\text{weight of the sulfonic-acid-form cation-exchange resin subjected to modification (g (wet state))})\}]\times 100$$

<Production of Bisphenol Compound>

A 0.50-g portion of the acidic catalyst obtained above was weighed out and put in an accessory test tube of personal organic-synthesis apparatus "Chemi Station PPV-3000", manufactured by Tokyo Rikakiki Co., Ltd. About 50 mL of 60° C. molten phenol was added thereto. This test tube was mounted in the apparatus, and nitrogen was introduced to stir the mixture and thereby wash the acidic catalyst with the phenol. Stirring and decantation were repeated until the phenol discharged after the washing came to have a water content of 0.1% by weight or less. Subsequently, 15.0 g of phenol was introduced into the test tube, and nitrogen and about 5° C. cooling water began to be passed. Thereafter, 0.71 g of acetone was added to initiate reaction while keeping the temperature of the liquid reaction mixture at 70° C. with stirring at 300 rpm.

After initiation of the reaction, the liquid reaction mixture was sampled at a given time interval, and the samples were analyzed by gas chromatography and ion chromatography under the following conditions to determine the yield of 4,4'-bisphenol A, the ratio of the amount of 4,4'-bisphenol A formed to the amount of 2,4'-bisphenol A formed (4,4'-isomer/2,4'-isomer ratio), and the amounts of phenyl acetate and acetic acid formed. The results thereof are shown in Table 3.

Incidentally, the terms "4,4'-bisphenol A" and "4,4'-isomer" mean 2,2-bis(4-hydroxyphenyl)propane, and the terms "2,4'-bisphenol A" and "2,4'-isomer" mean 2-(2-hydroxyphenyl)-2-(4-hydroxyphenyl)propane.

(Gas Chromatography)
Apparatus: "GC-2014", manufactured by Shimadzu Corp.
Column: "HP-Ultra 2" (25 m×0.32 mm×0.52 μm), manufactured by Agilent Technologies, Inc.
Detector: FID
Carrier gas: He (Calculation Method)

$$\text{Yield of 4,4'-bisphenol A (\%)}=[(\text{number of moles of the 4,4'-bisphenol A yielded})/(\text{number of moles of the acetone subjected to the reaction})]\times 100$$

$$\text{4,4'-Isomer/2,4'-isomer ratio}=[(\text{number of moles of the 4,4'-bisphenol A yielded})/(\text{number of moles of the 2,4'-bisphenol A yielded})]$$

(Ion Chromatography)

Method of pretreatment: A 1.0 g portion was weighed out of the liquid reaction mixture at 120 minutes after initiation of the reaction, and 0.5 g of cumene and 1 g of 0.1N sodium hydroxide aqueous solution were added thereto. The ingredients were mixed together by shaking. This mixture was allowed to stand still overnight, and the water phase only was collected.

Apparatus: (configured of the following devices)
Degasser: "DEGAS KT-27", manufactured by Showa Denko K.K.
Pumps (two): "LC-10AD" and "LC-10AT", manufactured by Shimadzu Corp.
Automatic injector: "AUTO SAMPLER 09", manufactured by System Instrument
Thermostatic chamber: "CTO-10A", manufactured by Shimadzu Corp.
Electrical-conductivity detector: "CD-5", manufactured by Showa Denko K.K.
Columns: "SPR-H" (250 mm×7.8 mm (diameter))$_{x2}$, manufactured by Shimadzu Corp.
Temperature: 45° C.
Eluents:
Liquid A: 5-mM aqueous p-toluenesulfonic acid solution
Liquid B: 20-mM Bis-Tris solution containing 100-μM 4H-EDTA

TABLE 3

| Reaction period (min) | Yield of 4,4'-bisphenol A (%) | 4,4'-Isomer/ 2,4'-isomer ratio | Amount of phenyl acetate formed (ppm) | Amount of acetic acid formed (ppm)* |
|---|---|---|---|---|
| 30 | 26 | 54 | not detectable | — |
| 60 | 40 | 50 | not detectable | — |
| 120 | 58 | 45 | not detectable | 11 |

*—: not determined

Example 4-1-2

Preparation of Acidic Catalyst

The same procedure as in Example 4-1-1 was conducted, except that the internal temperature of the flask during the dropping of 2-pyridylethyl thioacetate was changed to room temperature (25° C.). The amount of the acid in the filtrate obtained by separating the sulfonic-acid-form cation-exchange resin by filtration after completion of the modification and hydrolysis treatment was determined by titration analysis in the same manner as in Example 4-1-1. As a result, the acid amount was found to be 0.05 mmol. The conversion in hydrolysis of the 2-pyridylethyl thioacetate was 6.8%.

<Production of Bisphenol Compound>

Using the acidic catalyst, reaction was conducted under the same conditions as in Example 4-1-1. The liquid reaction mixture was sampled at a given time interval, and the samples were analyzed in the same manner as in Example 4-1-1 to determine the yield of 4,4'-bisphenol A, the 4,4'-isomer/2,4'-isomer ratio, and the amounts of phenyl acetate and acetic acid formed. The results thereof are shown in Table 4.

TABLE 4

| Reaction period (min) | Yield of 4,4'-bisphenol A (%) | 4,4'-Isomer/ 2,4'-isomer ratio | Amount of phenyl acetate formed (ppm) | Amount of acetic acid formed (ppm)* |
|---|---|---|---|---|
| 30 | 27 | 52 | 59 | — |
| 60 | 41 | 48 | 55 | — |
| 120 | 61 | 44 | 53 | 50 |

*—: not determined

Example 4-1-3

Preparation of Acidic Catalyst

A 0.50-g portion, in terms of wet-state amount, of a sulfonic-acid-form cation-exchange resin (DAIAION (registered trademark) "SK104H", manufactured by Mitsubishi Chemical Corp.; exchange capacity, 1.65 mmol/g (wet state)) was weighed and placed in an accessory test tube of personal organic-synthesis apparatus "Chemi Station PPV-3000", manufactured by Tokyo Rikakiki Co., Ltd. About 50 mL of 60° C. molten phenol was added thereto. This test tube was mounted in the apparatus, and the mixture was stirred while passing nitrogen to thereby wash the cation-exchange resin with the phenol. Stirring and decantation were repeated until the phenol discharged after the washing came to have a water content of 0.1% by weight or less. Subsequently, 15.0 g of phenol was introduced into the test tube, and nitrogen and about 5° C. cooling water began to be passed. Thereafter, the atmosphere in the flask was replaced with nitrogen while keeping the temperature of the liquid reaction mixture at 70° C., and stirring at 300 rpm was initiated. Subsequently, 0.023 g (0.13 mmol) of 2-pyridylethyl thioacetate prepared under the same conditions as in Example 4-1-1 was added dropwise with a syringe. After completion of the dropwise addition, the mixture was stirred for further 2 hours to conduct a modification treatment. Thus, an acidic catalyst (degree of modification, 15.8%) was prepared.

<Production of Bisphenol Compound>

While the test tube in which the acidic catalyst had been prepared was kept mounted in the apparatus, 0.71 g of acetone was introduced into the test tube to initiate reaction. After initiation of the reaction, the liquid reaction mixture was sampled at a given time interval, and the samples were analyzed in the same manner as in Example 4-1-1 to determine the yield of 4,4'-bisphenol A, the 4,4'-isomer/2,4'-isomer ratio, and the amounts of phenyl acetate and acetic acid formed. The results thereof are shown in Table 5.

TABLE 5

| Reaction period (min) | Yield of 4,4'-bisphenol A (%) | 4,4'-Isomer/ 2,4'-isomer ratio | Amount of phenyl acetate formed (ppm) | Amount of acetic acid formed (ppm)* |
|---|---|---|---|---|
| 30 | 25 | 53 | 418 | — |
| 60 | 40 | 49 | 405 | — |
| 120 | 56 | 45 | 375 | 220 |

*—: not determined

The results obtained in Examples 4-1-1 to 4-1-3 are summarized in Table 6.

TABLE 6

| | Modification hydrolysis atmosphere (solvent used) | Modification hydrolysis temperature (° C.) | Modification hydrolysis period (hr) | Degree of conversion in hydrolysis (%)* | Amount formed in reaction period of 120 minutes in bisphenol A production reaction (ppm) | |
|---|---|---|---|---|---|---|
| | | | | | Phenyl acetate | Acetic acid |
| Example 4-1-1 | water | 70 | 3 | 90.4 | not detectable | 11 |
| Example 4-1-2 | water | room temperature (25° C.) | 3 | 6.8 | 53 | 50 |
| Example 4-1-3 | phenol | 70 | 2 | — | 375 | 220 |

*—: not determined

As apparent from Table 6, the formation of impurities in the reaction for bisphenol A production was considerably reduced by using the catalysts obtained by hydrolyzing an acyl-protected compound.

Examples 4-2 to 4-13

An experiment was conducted in order to further investigate influences of modification (hydrolysis) temperature and modification (hydrolysis) period, the modification being conducted in a water solvent.

<Preparation of Acidic Catalyst>

Into an accessory test tube of personal organic-synthesis apparatus "Chemi Station PPV-3000", manufactured by Tokyo Rikakiki Co., Ltd, were introduced 1.00 g, in terms of wet-state amount, of a sulfonic-acid-form cation-exchange resin (DIAION (registered trademark) "SK104H", manufactured by Mitsubishi Chemical Corp.; exchange capacity, 1.65 mmol/g (wet state)) and about 20 mL of 60° C. desalted water. Stirring was initiated. While introducing nitrogen into the apparatus and keeping the internal temperature of the test tube at the given temperature shown in Table 7, 0.046 g (0.024 mmol) of 2-pyridylethyl thioacetate prepared under the same conditions as in Example 4-1 was added dropwise with a syringe. After completion of the dropwise addition, the mixture was further stirred for the given period shown in Table 7 to conduct modification and a hydrolysis treatment. Thereafter, the sulfonic-acid-form cation-exchange resin was taken out by filtration, and the amount of the acid in the filtrate and the conversion in hydrolysis of the 2-pyridylethyl thioacetate were determined in the same manners as in Example 4-1. The results thereof are shown in Table 7.

TABLE 7

| | Modification hydrolysis temperature (° C.) | Modification hydrolysis period (hr) | Acid amount (mmol) | Degree of conversion in hydrolysis (%) |
|---|---|---|---|---|
| Example 4-2 | 60 | 1 | 0.09 | 36 |
| Example 4-3 | 60 | 2 | 0.16 | 67 |
| Example 4-4 | 60 | 3 | 0.2 | 83 |
| Example 4-5 | 60 | 4 | 0.22 | 92 |
| Example 4-6 | 70 | 1 | 0.17 | 69 |
| Example 4-7 | 70 | 2 | 0.23 | 97 |
| Example 4-8 | 70 | 3 | 0.25 | 101 |
| Example 4-9 | 70 | 4 | 0.24 | 100 |
| Example 4-10 | 80 | 1 | 0.23 | 94 |
| Example 4-11 | 80 | 2 | 0.24 | 96 |
| Example 4-12 | 80 | 3 | 0.24 | 101 |
| Example 4-13 | 80 | 4 | 0.24 | 100 |

Figure 6:
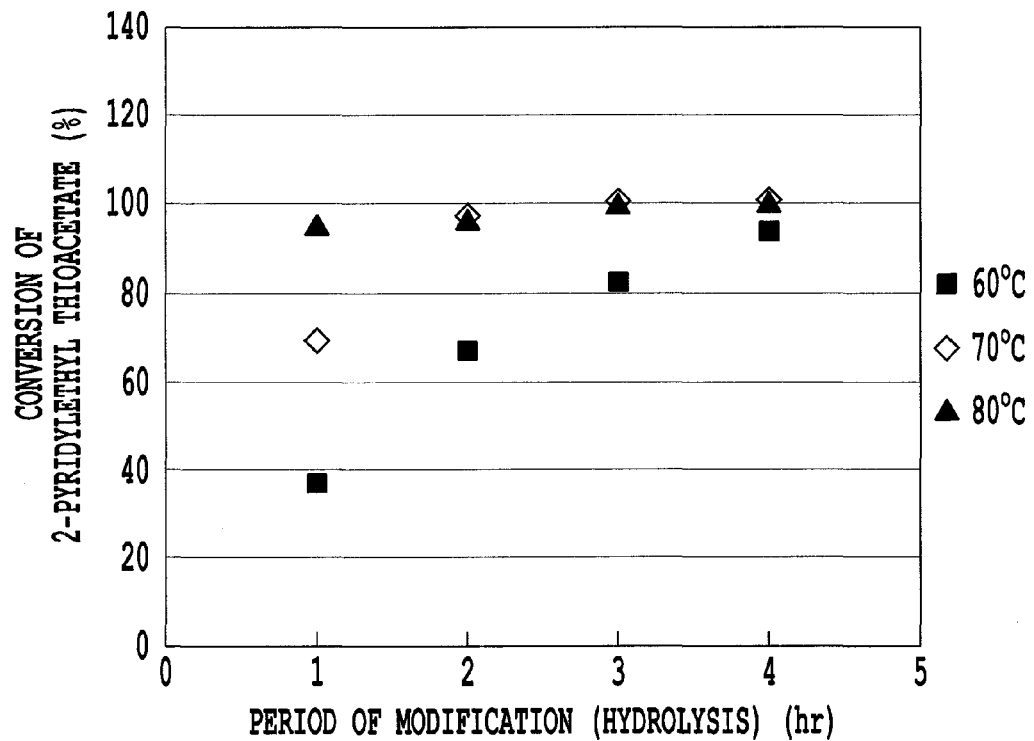
FIG. 6 is a presentation showing the relationships between modification (hydrolysis) temperature or modification (hydrolysis) period and the conversion in hydrolysis of 2-pyridylethyl thioacetate which were observed in Examples 4-2 to 4-13.

The relationships between modification (hydrolysis) temperature or modification (hydrolysis) period and the conversion in hydrolysis of the 2-pyridylethyl thioacetate, which were observed in Examples 4-2 to 4-13, are shown in FIG. 6.

It was found from the results obtained in Examples 4-2 to 4-13 that as the modification (hydrolysis) temperature rises, the rate of hydrolysis increases and the hydrolysis reaction comes to proceed in a shorter period.

This application is based on a Japanese patent application filed on Jan. 22, 2009 (Application No. 2009-012223), a Japanese patent application filed on Dec. 7, 2009 (Application No. 2009-277749), a Japanese patent application filed on Dec. 10, 2009 (Application No. 2009-280651), and a Japanese patent application filed on Dec. 11, 2009 (Application No. 2009-281781), the contents thereof being herein incorporated by reference.

INDUSTRIAL APPLICABILITY

According to the invention, an industrially advantageous process for stably producing a bisphenol compound with high conversion and high selectivity over a prolonged period can be provided.

The invention claimed is:

1. A process for producing a bisphenol compound which comprises:
    feeding a phenol compound and a carbonyl compound to a reactor packed with an acidic catalyst to produce the bisphenol compound,
    wherein the acidic catalyst is a sulfonic-acid-form cation-exchange resin in which part of the sulfo groups have been modified with at least any one of 2-pyridylalkanethiol compounds and 3-pyridylalkanethiol compounds and that the phenol compound and the carbonyl compound are continuously fed to the reactor packed with the acidic catalyst, and
    wherein at least part of the phenol compound is a phenol compound obtained when a bisphenol compound was purified, and wherein the phenol compound comprises phenol and at least one of bisphenol A, 2,4'-bisphenol A and p-isopropylphenol.

2. The process for producing a bisphenol compound as claimed in claim 1 wherein the acidic catalyst is a sulfonic-acid-form cation-exchange resin in which part of the sulfo groups have been modified with a 2-pyridylalkanethiol compound.

3. The process for producing a bisphenol compound as claimed in claim 1 wherein the 2-pyridylalkanethiol compound(s) is 2-pyridylethanethiol.

4. The process for producing a bisphenol compound as claimed in claim 3 wherein the 2-pyridylethanethiol is 2-pyridylethanethiol obtained from 2-vinylpyridine and a sulfur-containing compound as starting materials, and the content in the 2-vinylpyridine of 2-vinylpyridine-containing polymers which are the dimer and higher polymers is 2% by weight or less.

5. The process for producing a bisphenol compound as claimed in claim 4 wherein the content in the 2-vinylpyridine of 2-vinylpyridine-containing polymers which are the dimer and higher polymers is 100 weight ppm or higher.

6. The process for producing a bisphenol compound as claimed in claim 4 wherein the sulfur-containing compound is thiourea.

7. The process for producing a bisphenol compound as claimed in claim 3 wherein the 2-pyridylethanethiol is 2-pyridylethanethiol obtained by reacting 2-vinylpyridine with thiourea in the presence of water and a hydrocarbon solvent to obtain an isothiuronium salt and hydrolyzing the isothiuronium salt.

8. The process for producing a bisphenol compound as claimed in claimed 7 wherein the hydrocarbon solvent is toluene.

9. The process for producing a bisphenol compound as claimed in claim 1 wherein the acidic catalyst is a sulfonic-acid-form cation-exchange resin in which part of the sulfo groups have been modified with a 3-pyridylalkanethiol compound.

10. The process for producing a bisphenol compound as claimed in claim 1 wherein the 3-pyridylalkanethiol compound(s) is 3-pyridylethanethiol.

11. The process for producing a bisphenol compound as claimed in claim 1 wherein the acidic catalyst is an acidic catalyst obtained through the following steps (I) and (II):
    (I) a modification step in which a sulfonic-acid-form cation-exchange resin is modified using a compound obtained by protecting the thiol group of at least any one of 2-pyridylalkanethiol compounds and 3-pyridylalkanethiol compounds with an acyl group;
    (II) a hydrolysis step in which the thioester moiety of the compound obtained by protecting the thiol group of at least any one of 2-pyridylalkanethiol compounds and 3-pyridylalkanethiol compounds with an acyl group is hydrolyzed at a temperature of 40° C. to 100° C. during the modification and/or after the modification.

12. The process for producing a bisphenol compound as claimed in claim 11 wherein in step (II), the conversion of the compound obtained by protecting the thiol group of at least any one of 2-pyridylalkanethiol compounds and 3-pyridylalkanethiol compounds with an acyl group is 60% or higher.

13. The process for producing a bisphenol compound as claimed in claim 1 wherein the phenol compound is phenol, the carbonyl compound is acetone, and the bisphenol compound is bisphenol A.

14. The process for producing a bisphenol compound as claimed in claim 2 wherein the 2-pyridylalkanethiol compound(s) is 2-pyridylethanethiol.

15. The process for producing a bisphenol compound as claimed in claim 5 wherein the sulfur-containing compound is thiourea.

16. The process for producing a bisphenol compound as claimed in claim 6 wherein the 2-pyridylethanethiol is 2-pyridylethanethiol obtained by reacting 2-vinylpyridine with thiourea in the presence of water and a hydrocarbon solvent to obtain an isothiuronium salt and hydrolyzing the isothiuronium salt.

17. The process for producing a bisphenol compound as claimed in claim 9 wherein the 3-pyridylalkanethiol compound(s) is 3-pyridylethanethiol.

18. A process for producing a bisphenol compound which comprises:
feeding a phenol compound and a carbonyl compound to a reactor packed with an acidic catalyst to produce the bisphenol compound,
wherein the acidic catalyst is a sulfonic-acid-form cation-exchange resin in which part of the sulfo groups have been modified with at least any one of 2-pyridylalkanethiol compounds and 3-pyridylalkanethiol compounds and that the phenol compound and the carbonyl compound are continuously fed to the reactor packed with the acidic catalyst, and
wherein the phenol compound comprises 2,4'-bisphenol A in an amount of 0.3 parts by weight or more per 100 parts by weight of the phenol, and wherein the phenol compound comprises phenol and at least one of bisphenol A, 2,4'-bisphenol A and p-isopropylphenol.

19. The process for producing a bisphenol compound as claimed in claim 18 wherein the acidic catalyst is a sulfonic-acid-form cation-exchange resin in which part of the sulfo groups have been modified with a 2-pyridylalkanethiol compound.

20. The process for producing a bisphenol compound as claimed in claim 18 wherein the 2-pyridylalkanethiol compound(s) is 2-pyridylethanethiol.

21. The process for producing a bisphenol compound as claimed in claim 20 wherein the 2-pyridylethanethiol is 2-pyridylethanethiol obtained from 2-vinylpyridine and a sulfur-containing compound as starting materials, and the content in the 2-vinylpyridine of 2-vinylpyridine-containing polymers which are the dimer and higher polymers is 2% by weight or less.

22. The process for producing a bisphenol compound as claimed in claim 21 wherein the content in the 2-vinylpyridine of 2-vinylpyridine-containing polymers which are the dimer and higher polymers is 100 weight ppm or higher.

23. The process for producing a bisphenol compound as claimed in claim 21 wherein the sulfur-containing compound is thiourea.

24. The process for producing a bisphenol compound as claimed in claim 20 wherein the 2-pyridylethanethiol is 2-pyridylethanethiol obtained by reacting 2-vinylpyridine with thiourea in the presence of water and a hydrocarbon solvent to obtain an isothiuronium salt and hydrolyzing the isothiuronium salt.

25. The process for producing a bisphenol compound claimed in claim 24 wherein the hydrocarbon solvent is toluene.

26. The process for producing a bisphenol compound as claimed in claim 18 wherein the acidic catalyst is a sulfonic-acid-form cation-exchange resin in which part of the sulfo groups have been modified with a 3-pyridylalkanethiol compound.

27. The process for producing a bisphenol compound as claimed in claim 18 wherein the 3-pyridylalkanethiol compound(s) is 3-pyridylethanethiol.

28. The process for producing a bisphenol compound as claimed in claim 18 wherein the acidic catalyst is an acidic catalyst obtained through the following steps (I) and (II):
(I) a modification step in which a sulfonic-acid-form cation-exchange resin is modified using a compound obtained by protecting the thiol group of at least any one of 2-pyridylalkanethiol compounds and 3-pyridylalkanethiol compounds with an acyl group;

(II) a hydrolysis step in which the thioester moiety of the compound obtained by protecting the thiol group of at least any one of 2-pyridylalkanethiol compounds and 3-pyridylalkanethiol compounds with an acyl group is hydrolyzed at a temperature of 40° C. to 100° C. during the modification and/or after the modification.

29. The process for producing a bisphenol compound as claimed in claim 28 wherein in step (II), the conversion of the compound obtained by protecting the thiol group of at least any one of 2-pyridylalkanethiol compounds and 3-pyridylalkanethiol compounds with an acyl group is 60% or higher.

30. The process for producing a bisphenol compound as claimed in claim 18 wherein the phenol compound is phenol, the carbonyl compound is acetone, and the bisphenol compound is bisphenol A.

31. The process for producing a bisphenol compound as claimed in claim 18 wherein at least part of the phenol compound is a phenol compound obtained when a bisphenol compound was purified.

32. A process for producing a bisphenol compound which comprises:
feeding a phenol compound and a carbonyl compound to a reactor packed with an acidic catalyst to produce the bisphenol compound,
wherein the acidic catalyst is a sulfonic-acid-form cation-exchange resin in which part of the sulfo groups have been modified with at least any one of 2-pyridylalkanethiol compounds and 3-pyridylalkanethiol compounds and that the phenol compound and the carbonyl compound are continuously fed to the reactor packed with the acidic catalyst, and
wherein the phenol compound comprises p-isopropylphenol in an amount of 0.1 part by weight or more per 100 parts by weight of the phenol compound, and wherein the phenol compound comprises phenol and at least one of bisphenol A, 2,4'-bisphenol A and p-isopropylphenol.

33. The process for producing a bisphenol compound as claimed in claim 32 wherein the acidic catalyst is a sulfonic-acid-form cation-exchange resin in which part of the sulfo groups have been modified with a 2-pyridylalkanethiol compound.

34. The process for producing a bisphenol compound as claimed in claim 32 wherein the 2-pyridylalkanethiol compound(s) is 2-pyridylethanethiol.

35. The process for producing a bisphenol compound as claimed in claim 34 wherein the 2-pyridylethanethiol is 2-pyridylethanethiol obtained from 2-vinylpyridine and a sulfur-containing compound as starting materials, and the content in the 2-vinylpyridine of 2-vinylpyridine-containing polymers which are the dimer and higher polymers is 2% by weight or less.

36. The process for producing a bisphenol compound as claimed in claim 35 wherein the content in the 2-vinylpyridine of 2-vinylpyridine-containing polymers which are the dimer and higher polymers is 100 weight ppm or higher.

37. The process for producing a bisphenol compound claimed in claim 35 wherein the sulfur-containing compound is thiourea.

38. The process for producing a bisphenol compound as claimed in claim 34 wherein the 2-pyridylethanethiol is 2-pyridylethanethiol obtained by reacting 2-vinylpyridine with thiourea in the presence of water and a hydrocarbon solvent to obtain an isothiuronium salt and hydrolyzing the isothiuronium salt.

39. The process for producing a bisphenol compound claimed in claim 38 wherein the hydrocarbon solvent is toluene.

40. The process for producing a bisphenol compound as claimed in claim 32 wherein the acidic catalyst is a sulfonic-acid-form cation-exchange resin in which part of the sulfo groups have been modified with a 3-pyridylalkanethiol compound.

41. The process for producing a bisphenol compound as claimed in claim 32 wherein the 3-pyridylalkanethiol compound(s) is 3-pyridylethanethiol.

42. The process for producing a bisphenol compound as claimed in claim 32 wherein the acidic catalyst is an acidic catalyst obtained through the following steps (I) and (II):

(I) a modification step in which a sulfonic-acid-form cation-exchange resin is modified using a compound obtained by protecting the thiol group of at least any one of 2-pyridylalkanethiol compounds and 3-pyridylalkanethiol compounds with an acyl group;

(II) a hydrolysis step in which the thioester moiety of the compound obtained by protecting the thiol group of at least any one of 2-pyridylalkanethiol compounds and 3-pyridylalkanethiol compounds with an acyl group is hydrolyzed at a temperature of 40° C. to 100° C. during the modification and/or after the modification.

43. The process for producing a bisphenol compound as claimed in claim 42 wherein in step (II), the conversion of the compound obtained by protecting the thiol group of at least any one of 2-pyridylalkanethiol compounds and 3-pyridylalkanethiol compounds with an acyl group is 60% or higher.

44. The process for producing a bisphenol compound as claimed in claim 32 wherein the phenol compound is phenol, the carbonyl compound is acetone, and the bisphenol compound is bisphenol A.

45. The process for producing a bisphenol compound as claimed in claim 32 wherein at least part of the phenol compound is a phenol compound obtained when a bisphenol compound was purified.

* * * * *